(12) United States Patent
Barrier et al.

(10) Patent No.: US 8,920,433 B2
(45) Date of Patent: Dec. 30, 2014

(54) ERGONOMIC AND SEMI-AUTOMATIC MANIPULATOR, AND APPLICATIONS TO INSTRUMENTS FOR MINIMALLY INVASIVE SURGERY

(75) Inventors: Pascal Barrier, Annecy (FR); Jérémy Ollagnier, Meythet (FR); Rémi Rosset-Lanchet, Annecy (FR); Christine Melennec épouse Barthod, Naves Parmelan (FR); Max Giordano, Annecy le Vieux (FR)

(73) Assignee: Dexterite Surgical, Annecy (FR)

( * ) Notice: Subject to any disclaimer, the term of this patent is extended or adjusted under 35 U.S.C. 154(b) by 364 days.

(21) Appl. No.: 13/387,773

(22) PCT Filed: Jul. 30, 2010

(86) PCT No.: PCT/IB2010/053477
§ 371 (c)(1),
(2), (4) Date: Jan. 30, 2012

(87) PCT Pub. No.: WO2011/013103
PCT Pub. Date: Feb. 3, 2011

(65) Prior Publication Data
US 2012/0130401 A1 May 24, 2012

(30) Foreign Application Priority Data
Jul. 31, 2009 (FR) ..................................... 09 55382

(51) Int. Cl.
| | |
|---|---|
| A61B 19/00 | (2006.01) |
| A61B 17/00 | (2006.01) |
| B25J 17/00 | (2006.01) |
| A61B 17/29 | (2006.01) |
| A61B 17/34 | (2006.01) |
| A61B 17/062 | (2006.01) |

(52) U.S. Cl.
CPC ............. *A61B 19/22* (2013.01); *A61B 17/2909* (2013.01); *A61B 17/3421* (2013.01); *A61B 17/3423* (2013.01); *A61B 2017/00424* (2013.01); *A61B 2017/291* (2013.01); *A61B 2017/2927* (2013.01); *A61B 2017/2929* (2013.01); *A61B 2019/2269* (2013.01); *A61B 17/062* (2013.01)
USPC .......................... 606/130; 606/207; 74/490.05

(58) Field of Classification Search
USPC .................. 606/130, 139, 205, 206, 208, 207
See application file for complete search history.

(56) References Cited

U.S. PATENT DOCUMENTS 5,354,313 A * 10/1994 Boebel ........................... 606/208
5,797,900 A * 8/1998 Madhani et al. .................. 606/1

(Continued)

FOREIGN PATENT DOCUMENTS

JP 2001276091 10/2001

*Primary Examiner* — Tuan V Nguyen
(74) *Attorney, Agent, or Firm* — William H. Eilberg

(57) ABSTRACT

A manipulator includes a control unit (1), with handle (4) and control buttons (4a-4d), and a connecting arm (2) which, at its proximal end (2a), carries the control unit (1) and, at its distal end (2b), carries a work unit (3). The control buttons (4a-4d) control at least a first inclination motor, which causes a movement of inclination of a tool support (5) of the work unit (3) about a transverse inclination axis (11), and they control the actual rotation of the tool support (5) about its direction of inclination (II) and control the orientation of the direction of inclination (II) about the longitudinal axis (I-I) of the connecting arm (2). A particularly ergonomic manipulator is thus obtained which is easy to learn to use and which efficiently separates the stresses arising from movements of the tool support (5) and the stresses arising from holding and moving the manipulator itself.

16 Claims, 23 Drawing Sheets

(56) References Cited

U.S. PATENT DOCUMENTS

| | | | |
|---|---|---|---|
| 6,889,119 B2* | 5/2005 | Riff et al. | 700/254 |
| 7,942,895 B2* | 5/2011 | Jinno et al. | 606/205 |
| 8,613,740 B2* | 12/2013 | Barrier et al. | 606/1 |
| 2002/0040217 A1 | 4/2002 | Jinno | |
| 2004/0260334 A1 | 12/2004 | Braun | |
| 2005/0222587 A1 | 10/2005 | Jinno | |
| 2006/0190027 A1* | 8/2006 | Downey | 606/205 |
| 2008/0039255 A1 | 2/2008 | Jinno | |

\* cited by examiner

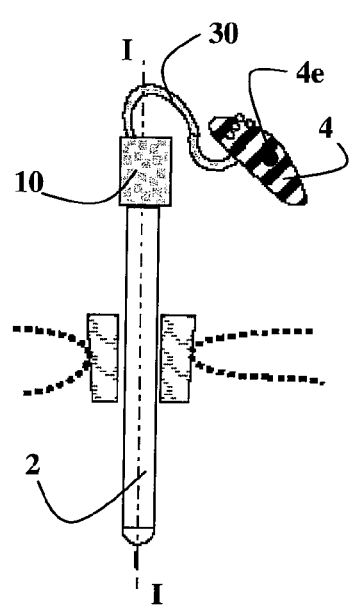
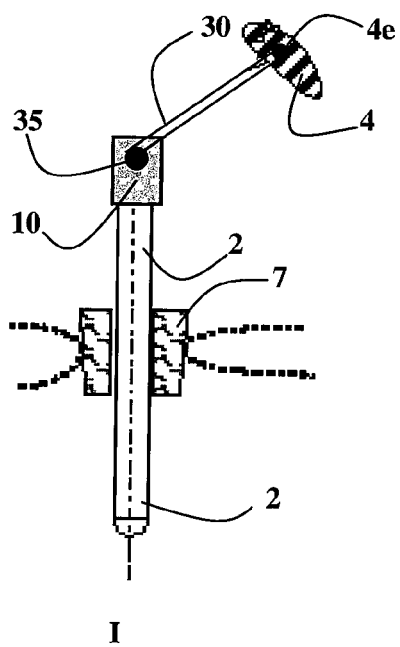
FIG. 25  FIG. 26
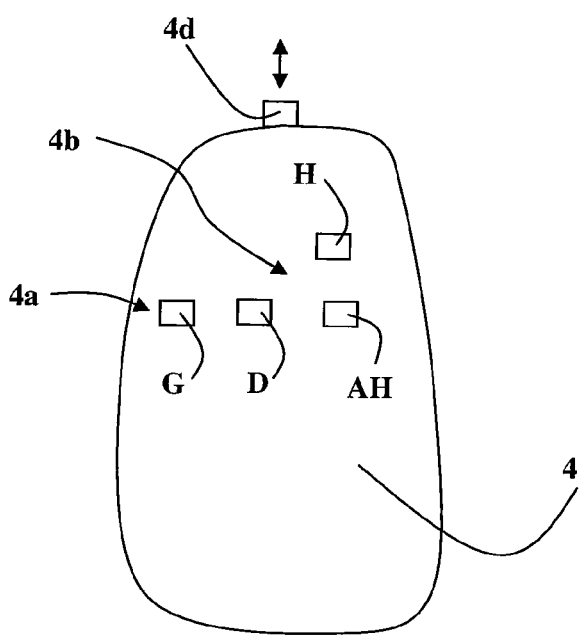
FIG. 27

ERGONOMIC AND SEMI-AUTOMATIC MANIPULATOR, AND APPLICATIONS TO INSTRUMENTS FOR MINIMALLY INVASIVE SURGERY

TECHNICAL FIELD OF THE INVENTION

The present invention relates to devices for guidance and manipulation, permitting the movements of a manipulation instrument located inside the operating area to be controlled from outside an operating area.

In particular, said devices for guidance and manipulation permit a surgical instrument to be controlled in applications for minimally-invasive surgery carried out by endoscopy.

In said applications, it is necessary to be able to displace and control a surgical instrument to carry out various operations such as providing a suture, tying a knot or delicate dissection of tissue. These are intricate, precise operations in which the movements to be carried out are complex.

Devices for guidance and manipulation by remote-controlled robot have already been proposed, for example the device disclosed in the document U.S. Pat. No. 5,797,900. In this case, a master arm which is able to be actuated by an operator is completely mechanically separated and remote from a slave arm which carries the surgical instrument. The slave arm is carried by a support in the vicinity of the operating table. The master arm is located on a remote control unit, provided with means for visualization, the two units being connected by lines for transmitting visualization signals and control signals. Such a device is particularly complex, costly and bulky, comprising a remote manipulation unit for remote control of a slave unit carrying the surgical instrument.

The invention relates more specifically to portable devices for guidance and manipulation, in which the surgical instrument is placed at the end of a portable manipulator, essentially having a connecting arm with a proximal end and a distal end. Portable manipulators are known in which the proximal end of the connecting arm carries a control unit having a handle capable of being held by one hand. Control members, mounted on the handle, are capable of being actuated by at least one finger of the hand holding the handle. A working unit is mounted on the distal end of the connecting arm, and comprises a tool support capable of supporting a surgical tool.

The tool support is mounted in a manner in which it is able to be inclined in the working unit relative to the connecting arm, by rotation about a transverse inclination axis. The control members thus make it possible to control the orientation of the tool support in a direction of inclination by rotation about the transverse inclination axis. The control members also permit the orientation of the direction of inclination about the longitudinal axis of the connecting arm to be controlled, in order to communicate to the tool an orientation which is able to be selected within a cone about the longitudinal axis of the connecting arm. The control members also make it possible to control the specific rotation of the tool support about the direction of inclination.

Such a device is disclosed, for example, in the document US 2005/0222587 A1 and comprises:

a control unit, having a handle capable of being held by one hand,
control members mounted on the handle and capable of being actuated by at least one finger of the hand holding the handle,
a connecting arm extending along a longitudinal axis, having a proximal end in which the control unit is mounted, and having a distal end,
a working unit mounted on the distal end of the connecting arm and comprising a tool support capable of supporting a tool,
the tool support being mounted in a manner in which it may be inclined in the working unit relative to the connecting arm by rotation about a transverse inclination axis,
the control members make it possible to control the transverse inclination of the tool support in a direction of inclination by rotation about the transverse inclination axis,
the control members make it possible to control the specific rotation of the tool support about the direction of inclination;
furthermore:
in its transverse inclined rotation, the tool support is driven by at least one first inclination actuator controlled by a first of the control members of the handle,
in the specific rotational movement of the tool support about the direction of inclination, the manipulator is controlled by a second of the control members of the handle which controls one or more actuators,
in the movement of orientation of the direction of inclination about the longitudinal axis of the connecting arm, the manipulator is controlled to perform a rotation about the longitudinal axis, by the handle being urged in rotation by a motorized drive member relative to the remainder of the manipulator about the longitudinal axis of the connecting arm.

Due to the use of actuators controlled by control members arranged on the handle, the hand holding the handle is able to carry the manipulator and hold it in a position which is well-defined and easily controllable by the operator, who thus controls the position of the surgical tool in a natural manner. At the same time, the specific movements of rotation and inclination of the tool support at the end of the manipulator are controlled by the actuation of the control members mounted on the handle, and said control members may be activated by movements of low force and low amplitude of the fingers of the hand holding the handle, providing an effective disassociation between holding the manipulator to fix the position of the surgical tool and controlling the movements of the tool support about its position defined by the position of the manipulator.

At the same time, the different potential movements for orienting the direction of inclination about the longitudinal axis of the connecting arm make it possible to provide the tool with any necessary positions within a cone extending the connecting arm.

SUMMARY OF THE INVENTION

It has, however, been shown that with such a device the transmission of the different movements of the tool carrier is bulky, in particular by the arrangement of a plurality of joints in cascade along the longitudinal axis, and also because no means is provided to carry out all the transmissions of movement within a small diameter of the distal part of the manipulator. Thus a need exists to design further transmission means, simultaneously providing reduced bulk and sufficient rigidity of the transmissions which require it.

To achieve this, the present invention provides that the specific rotational movements and possible opening-closing movements of the forceps are transmitted to the tool support by gears and tubes or shafts housed in the working unit, whilst the inclination movements about the transverse axis are transmitted by cables.

One advantage of the gears and tubes or shafts is to provide a rigid transmission of forces for the movements which require this feature, whilst the transmission by cables for the inclination movement makes it possible at the same time to reduce the bulk of the device.

In practice, it is advantageously possible to provide that the specific rotational movement of the tool support is provided by an input tube, in turn driven in rotation by a specific rotation actuator and carrying a conical end pinion which itself drives in rotation a lateral conical pinion rotating about a transverse axis and which drives an axial conical pinion fixed to the tool support.

Similarly, it is also possible to provide that the tool is forceps and that:
  a forceps actuator is coupled to an axial input shaft oriented along the longitudinal axis of the connecting arm,
  the axial input shaft carries a conical end pinion which drives a lateral conical pinion rotating about a transverse axis and driving a conical pinion mounted at the end of the axially threaded and wedged output shaft on which is mounted a nut fixed to a mobile jaw of the tool.

Said arrangement makes it possible to provide a high clamping force which is useful, in particular, when the forceps is a needle holder.

In the case of forceps, it is also advantageous to provide that the forceps comprise a fixed jaw and a mobile jaw: the fixed jaw facilitates the positioning of a needle before closing the mobile jaw.

In the case of a tool in the form of forceps, it is also possible to provide that the tool support comprises an arched portion pivotably mounted about a transverse axis on the distal end of the connecting arm and fixed to a pulley urged in rotation by a cable which is itself activated by an inclination actuator.

To improve further the disassociation between controlling the specific rotational movement of the tool support and all the other movements of the tool support and, in particular, holding the manipulator in position, it is advantageously possible to provide that the second of the control members comprises a first input member, of which the actuation causes the specific rotation of the tool support in a first rotational direction and a second input member, of which the actuation causes the specific rotation of the tool support in the second rotational direction. Thus the operator is provided with a great facility for inclining the tool support at the end of the connecting arm by natural movements of the fingers of the hand.

According to an advantageous embodiment, the first of the control members may comprise a third input member, of which the activation causes a positive increase in the inclination angle, and a fourth input member, of which the activation causes a negative increase in the inclination angle.

According to a first embodiment, the input members of the first and second control members may be of the "all or nothing" type and may each control the movement of the tool support in one respective direction according to a substantially constant rotational speed.

Alternatively, it is possible to provide that the input members are of the progressive type, each controlling the movement of the tool support according to a rotational speed which is variable between a rapid speed and a slow speed. Thus a good compromise is achieved between the speed of actuation and the precision.

Preferably, it is possible to provide that the input members are of the "all or nothing" type in stepped mode, changing to continuous mode at higher speeds by maintaining the activation.

More advantageously, it is possible to provide that the first of the control members also has the potential for activating resetting, which returns the tool support into the axis of the support arm. In this manner, the operator is provided with an excellent facility for locating the position from the neutral position at the end of the connecting arm.

In the case of a forceps-type tool, advantageously the manipulator may also comprise on the handle a forceps control member, of which the actuation controls at least one forceps actuator which selectively causes the opening and closing of the forceps. Thus the actuation of the forceps is also implemented by a simple movement of a finger of the hand, without interfering with holding the manipulator and with the other movements of the tool support.

In this case, the forceps control member may comprise, in particular, a first open forceps position, at least one second forceps position closed by light clamping and at least one third forceps position closed by strong clamping.

In addition or alternatively, it is possible also to provide an actuator for rotating the arm, carrying out the specific rotation of the connecting arm about its longitudinal axis relative to the handle, said actuator for specifically rotating the arm being controlled by the third control member of the handle.

According to a further advantageous embodiment, the manipulator may comprise a positioning arm between the handle and the connecting arm, and by which the operator can modify and fix the angular and/or spatial position relative to the handle with regard to the connecting arm.

BRIEF DESCRIPTION OF THE DRAWINGS

Further subjects, features and advantages of the present invention will emerge from the following description of particular embodiments, made with reference to the accompanying figures, in which:

FIG. 25 illustrates schematically a manipulator according to a further embodiment of the invention, with a deformable connection between the handle and the body of the manipulator;

FIG. 26 illustrates a further embodiment of the manipulator according to the invention, with an articulated connection between the handle and the body of the manipulator; and FIG. 27 illustrates an example of positioning the input members on a handle.

DESCRIPTION OF PREFERRED EMBODIMENTS

Figure 1:
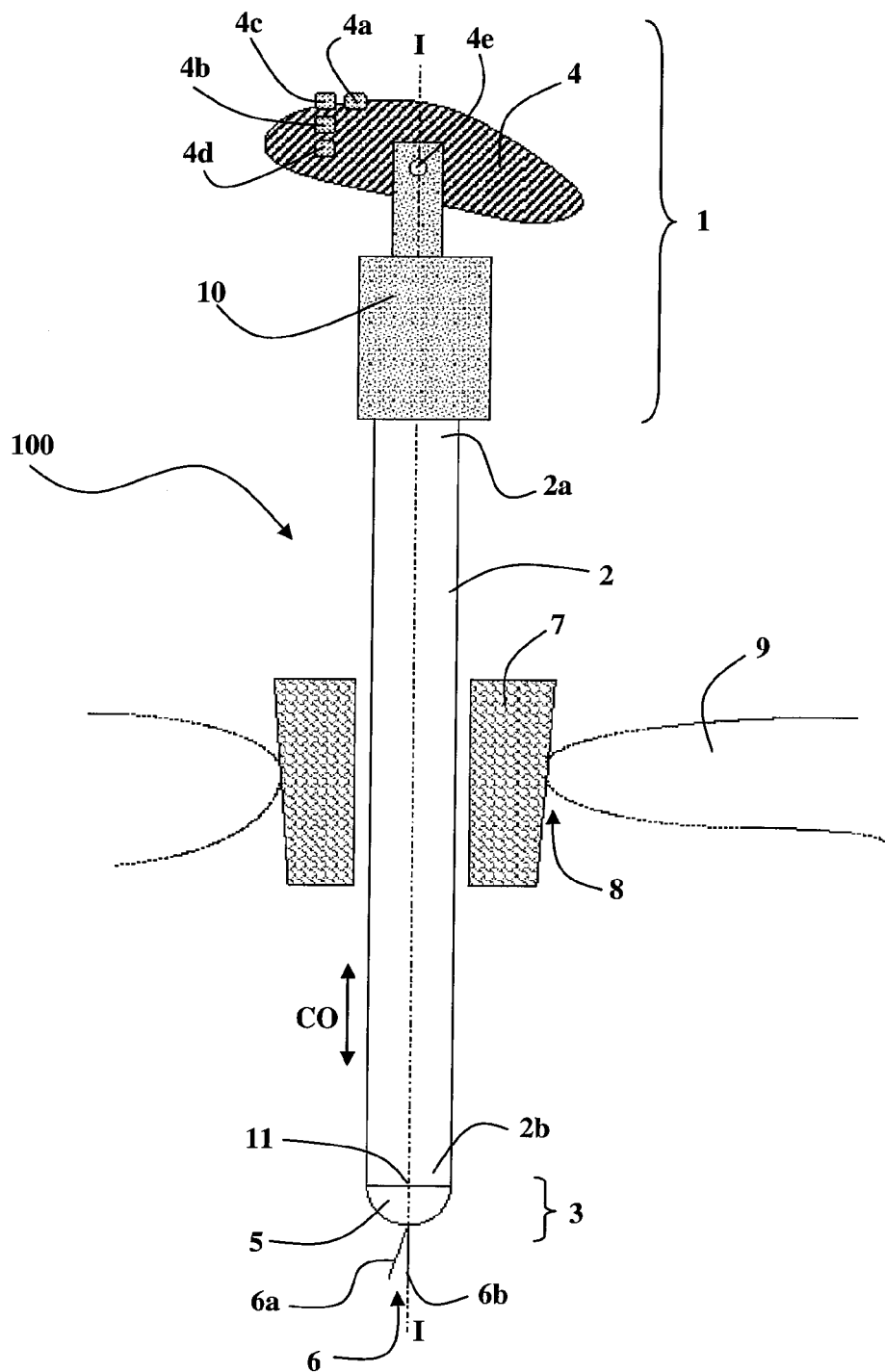
FIG. 1 is a basic sketch illustrating the overall structure of a manipulator according to an embodiment of the present invention in the position of use.
Figure 2:
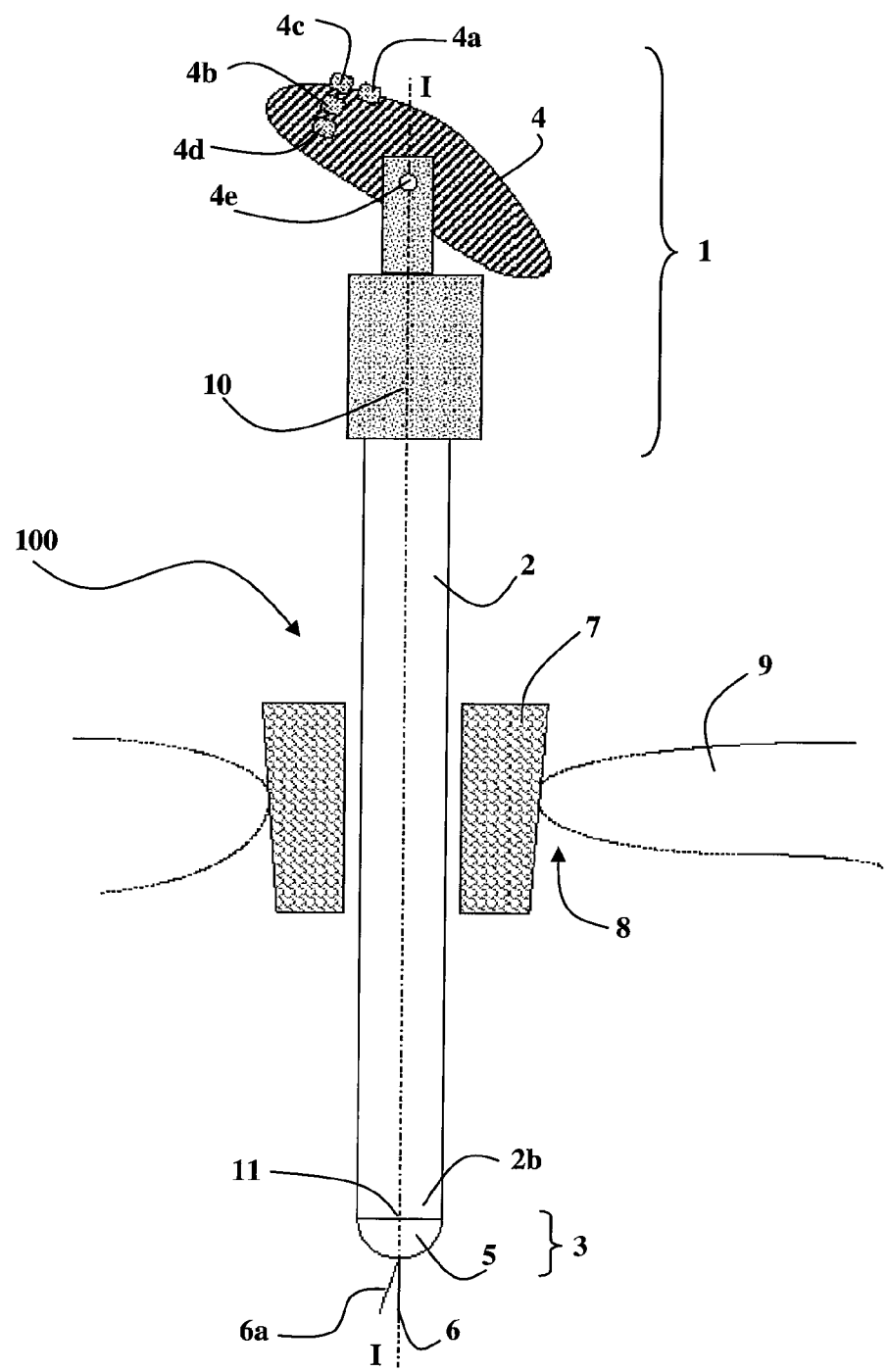
FIG. 2 illustrates the manipulator of FIG. 1, with the handle slightly pivoted.
Figure 3:
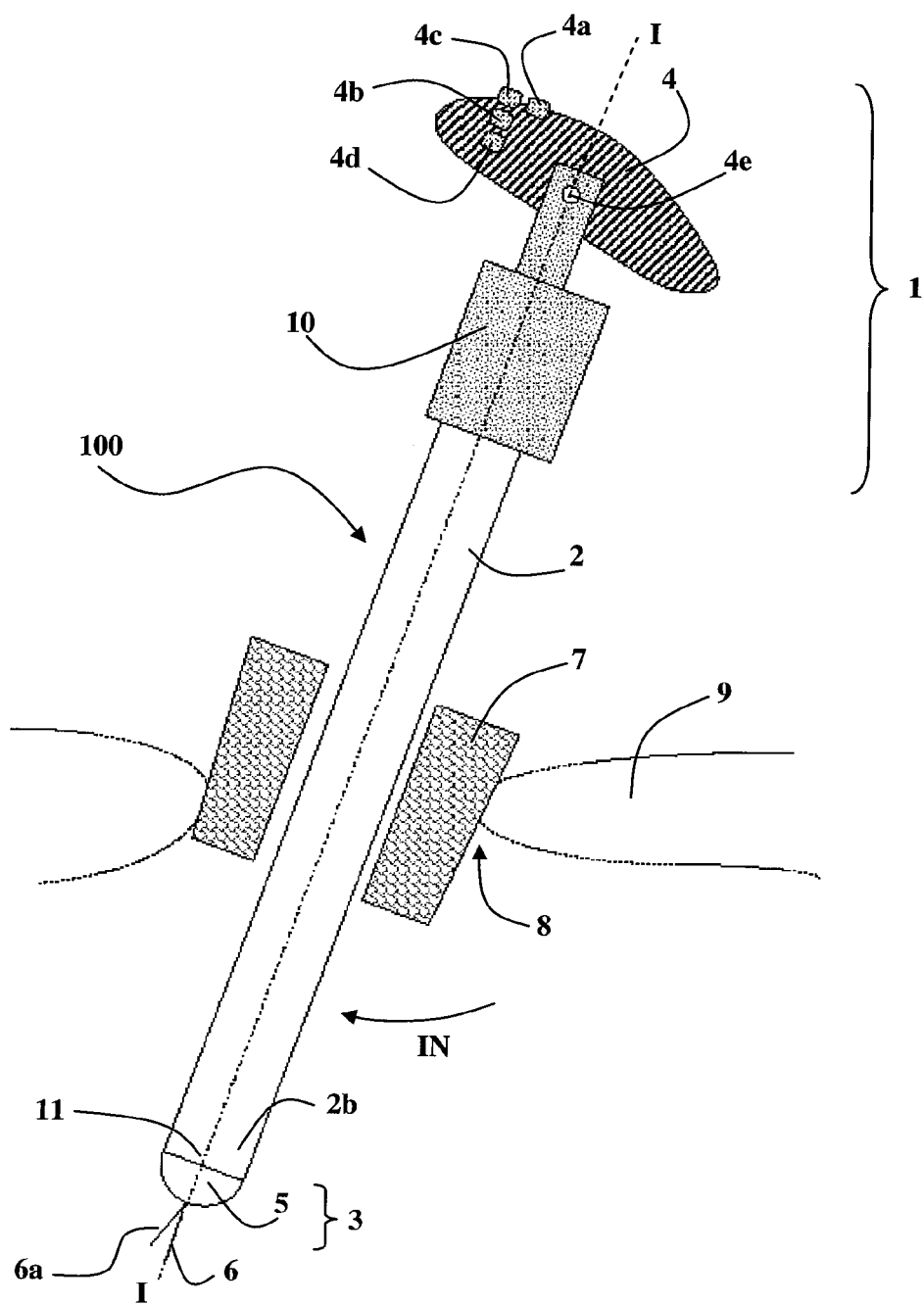
FIG. 3 illustrates the manipulator of FIG. 1 in the position pivoted about the trocar.
Figure 4:
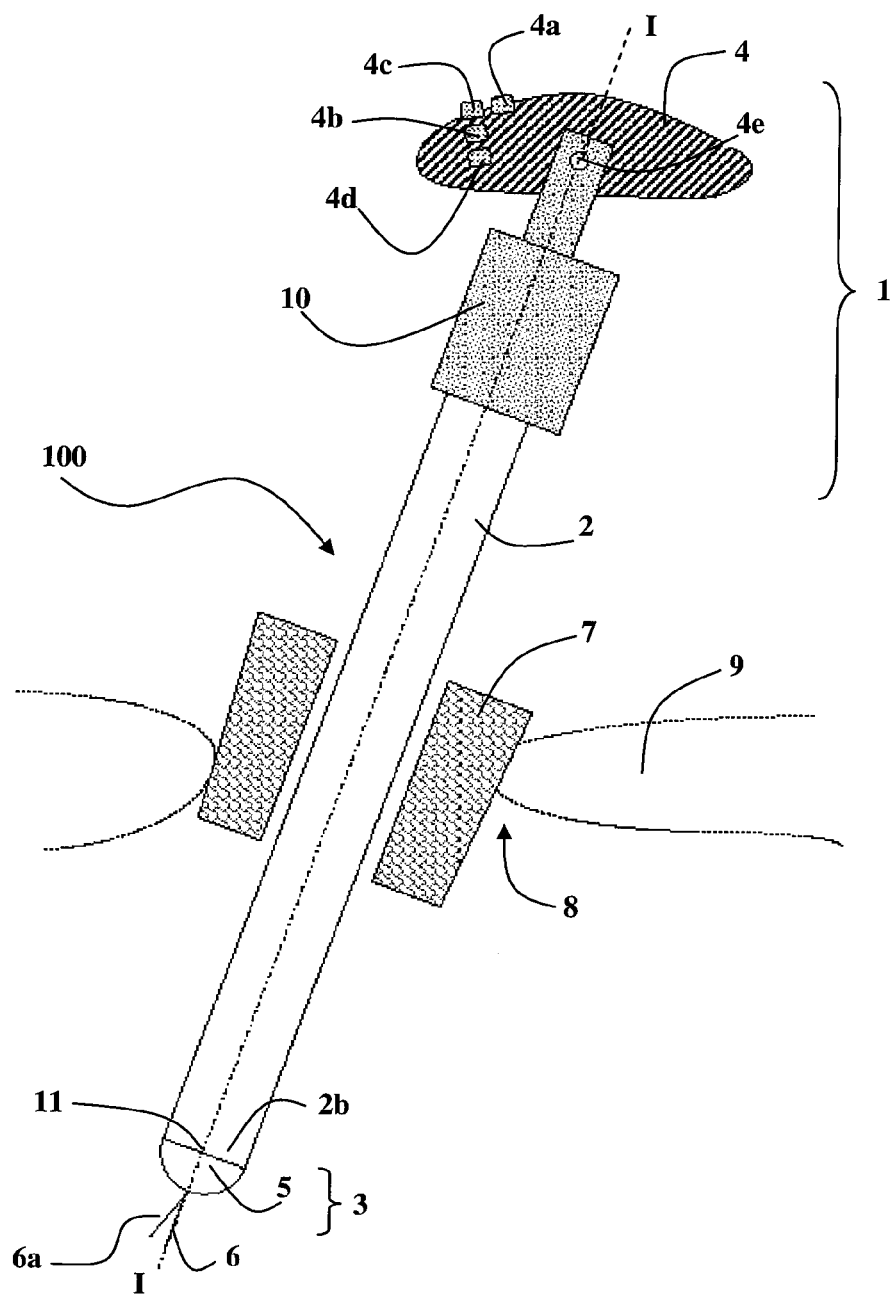
FIG. 4 is a schematic view of the manipulator of FIG. 3 with the handle pivoted.

Firstly, the overall structure of a manipulator according to the invention is considered, as illustrated in FIGS. 1 to 12.

Such a manipulator 100 generally comprises a control unit 1, a connecting arm 2 and a working unit 3.

The control unit 1 is mounted on the proximal end 2a of the connecting arm 2 whilst the working unit 3 is mounted on the distal end 2b of the connecting arm 2.

The control unit 1 comprises a handle 4 capable of being held by one hand of an operator, and a control body 10 containing various drive means to produce the appropriate movements in the working unit 3.

The working unit 3 comprises a tool support 5 capable of supporting a tool 6. In the figures, a tool 6 has been illustrated in the form of forceps with two arms 6a and 6b.

The handle 4 comprises control members, for example a first control member 4a, a second control member 4b, a third control member 4c and a forceps control member 4d.

As in the known devices, the connecting arm 2 passes into a trocar 7 providing the connection and passage into an opening 8 formed in the body wall 9. The control unit 1 remains outside the body of the patient, whilst the working unit 3 penetrates inside the body of the patient to reach the operating area where the tool 6 has to carry out movements controlled by the control unit 1.

In FIGS. 1 to 4, the tool 6 and the tool support 5 are in alignment with the longitudinal axis I-I of the connecting arm 2. As may be seen in these figures, the operator is able to position the working unit in a precise manner in the operating area by the sliding CO of the connecting arm 2 into the trocar 7 and by the inclination IN of the connecting arm 2 and of the trocar 7 in the opening 8 of the body wall 9.

Figure 5:
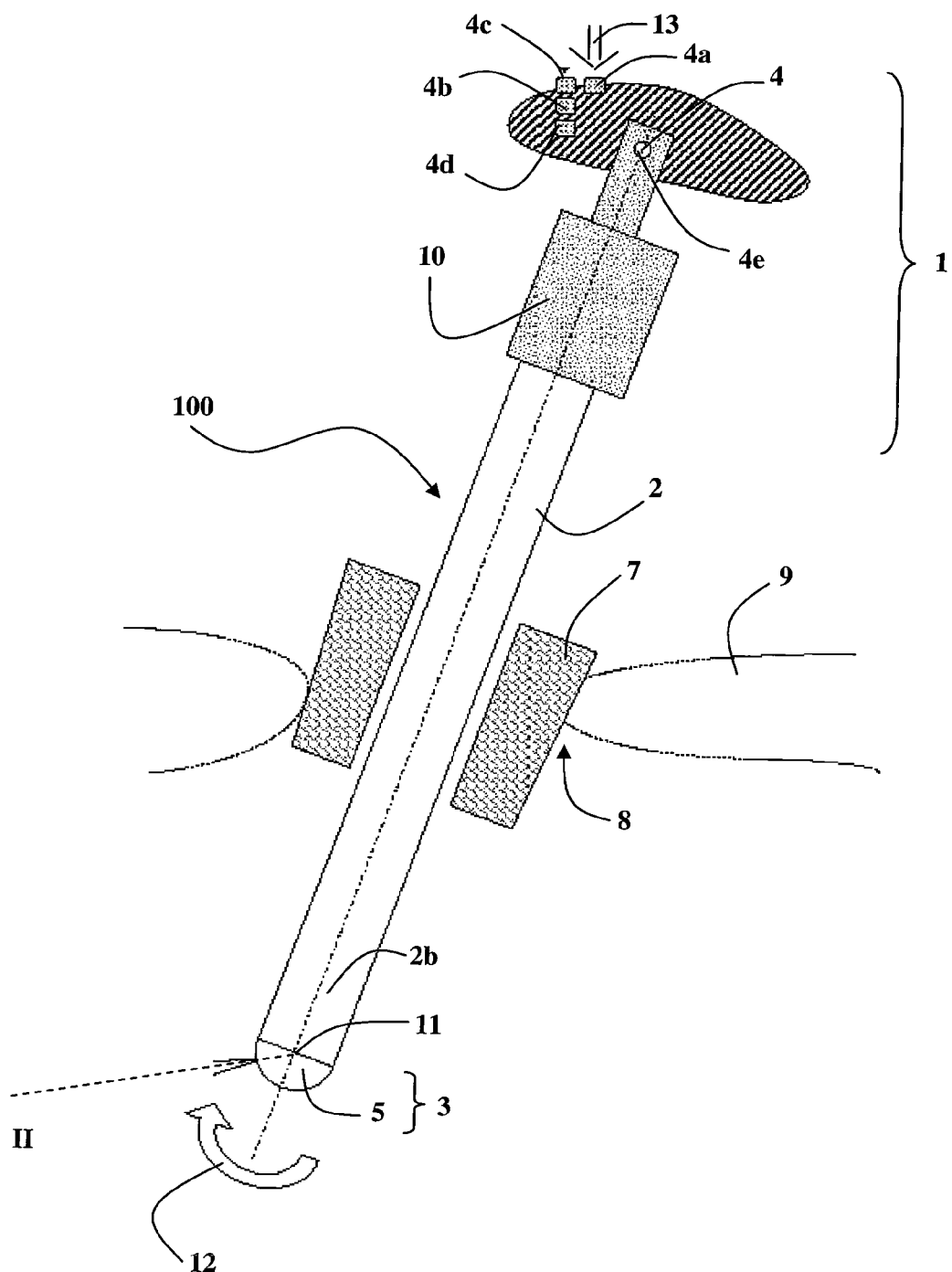
FIG. 5 is an overall view of the manipulator of the preceding figures, illustrating the inclination movement of the tool support.

In FIG. 5, a first movement of the tool support 5 has been illustrated, namely an inclined movement 12 about a transverse axis of inclination 11. Said movement is obtained by the activation 13 of the first control member 4a of the handle 4 which controls an inclination actuator housed in the control body 10. By way of illustration, it is possible to refer to FIG. 17, illustrating the inclination actuator 40a which is connected to the working unit 3 by an inclination transmission cable 41a illustrated in FIG. 15.

In FIG. 5, by actuation 13 of the first control member 4a, the tool support 5 has been inclined to orientate it in a direction of inclination II.

Figure 6:
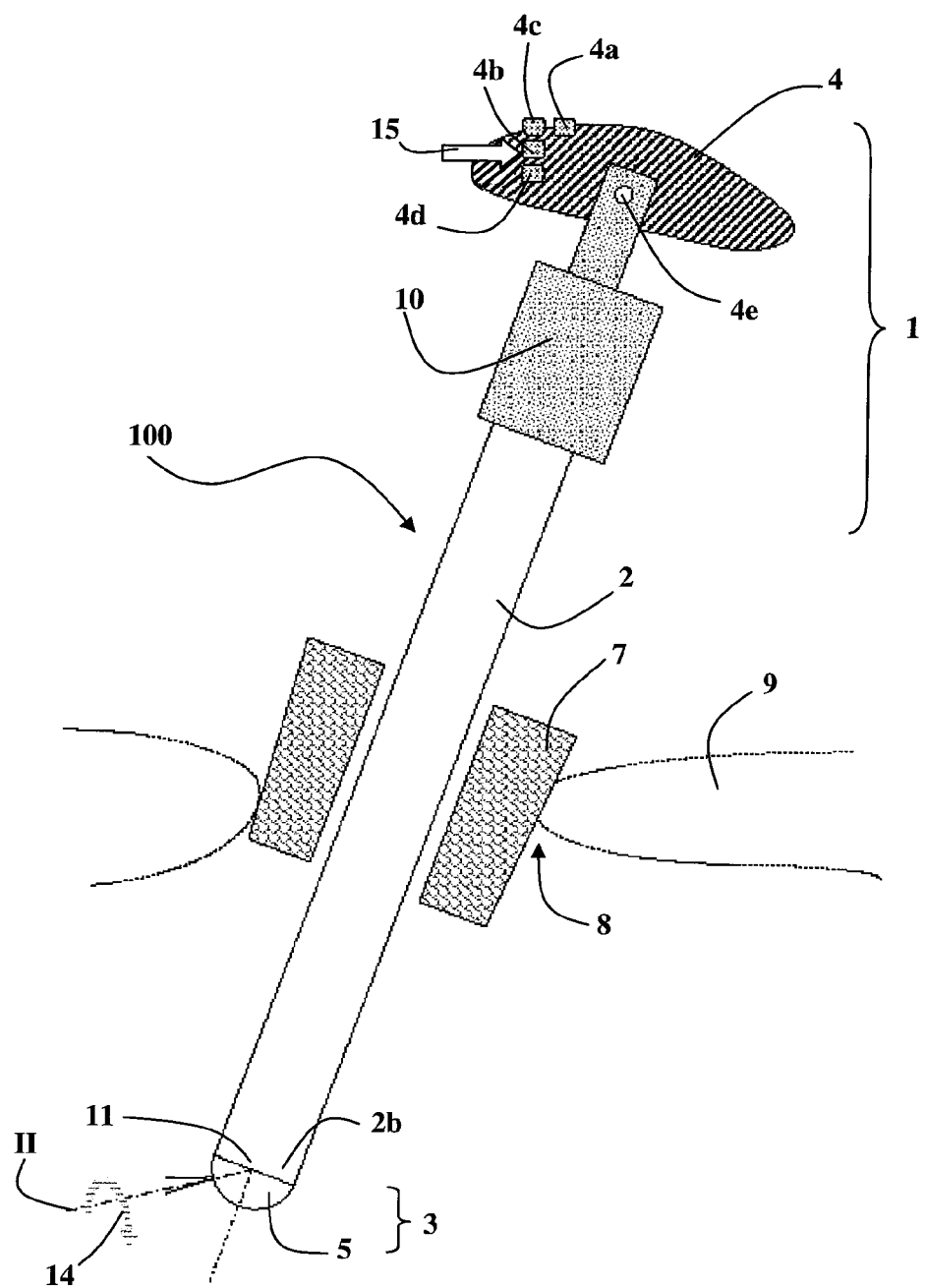
FIG. 6 illustrates the specific rotational movement of the tool support.

Now FIG. 6 will be considered, which illustrates a second movement of the tool support 5, namely a specific rotational movement 14 about the direction of inclination II. Said specific rotational movement 14 of the tool support 5 about the direction of inclination II is obtained by an activation 15 of the second control member 4b which controls one or more inclination actuators housed in the control body 10.

Figure 17:
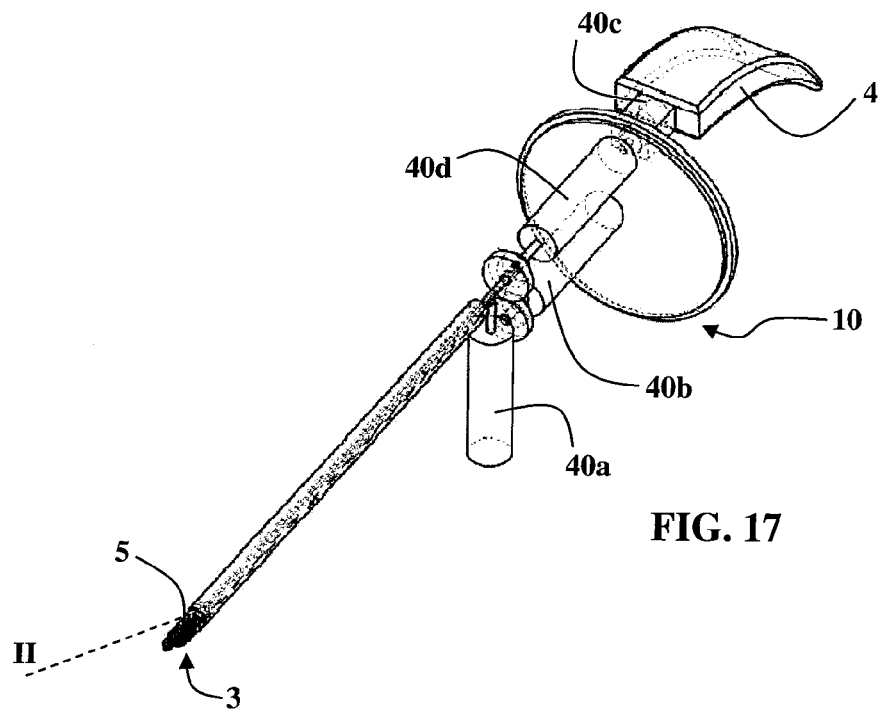
FIG. 17 is a perspective view of the manipulator of FIG. 16, with the cap of the control unit removed.

The generation of specific rotational movements 14 may advantageously be implemented according to the invention by the activation 15 of the second control member 4b of the handle 4 which controls a specific rotation actuator 40b housed in the control body 10 (FIG. 17).

Figure 7:
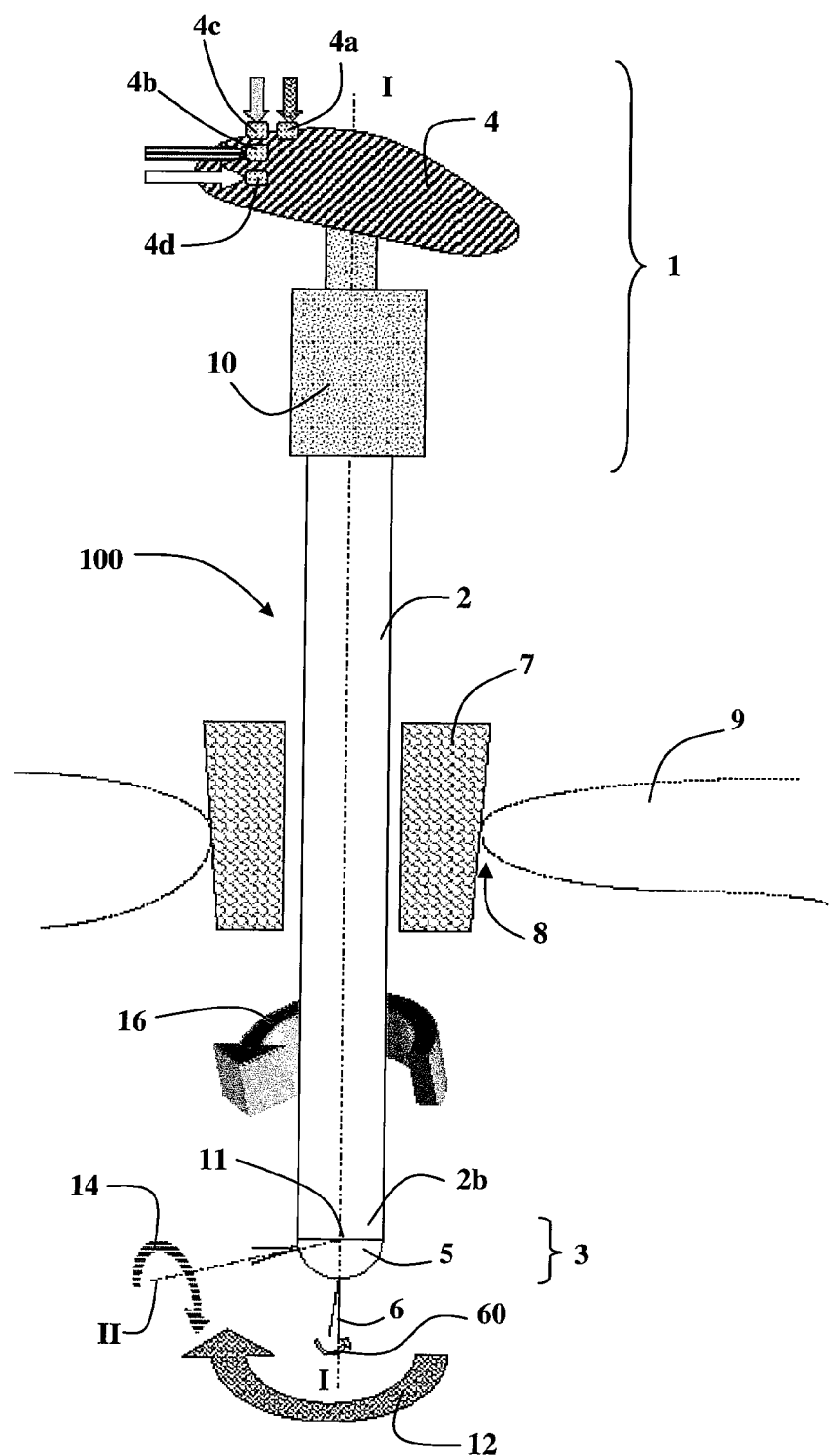
FIG. 7 illustrates an embodiment of the manipulator of the preceding figures and shows the different movements of the tool.

Now FIG. 7 will be considered, which illustrates a further movement of the tool support 5, namely a movement by which the direction of inclination II is oriented about the longitudinal axis I-I of the connecting arm 2. Said orientation movement is illustrated by the arrow 16.

According to the invention, it is possible to produce said orientation movement 16 either by causing the specific relative rotation of the connecting arm 2 about its longitudinal axis I-I relative to the handle 4, or by a manipulation of the handle 4 for a rotation of the entire manipulator about the longitudinal axis I-I of the connecting arm 2.

In the first case, the rotation of the connecting arm 2 is obtained by the activation of the third control member 4c of the handle 4 which controls an actuator for rotating the arm 40c housed in the control body 10 (FIG. 17).

Figure 22:
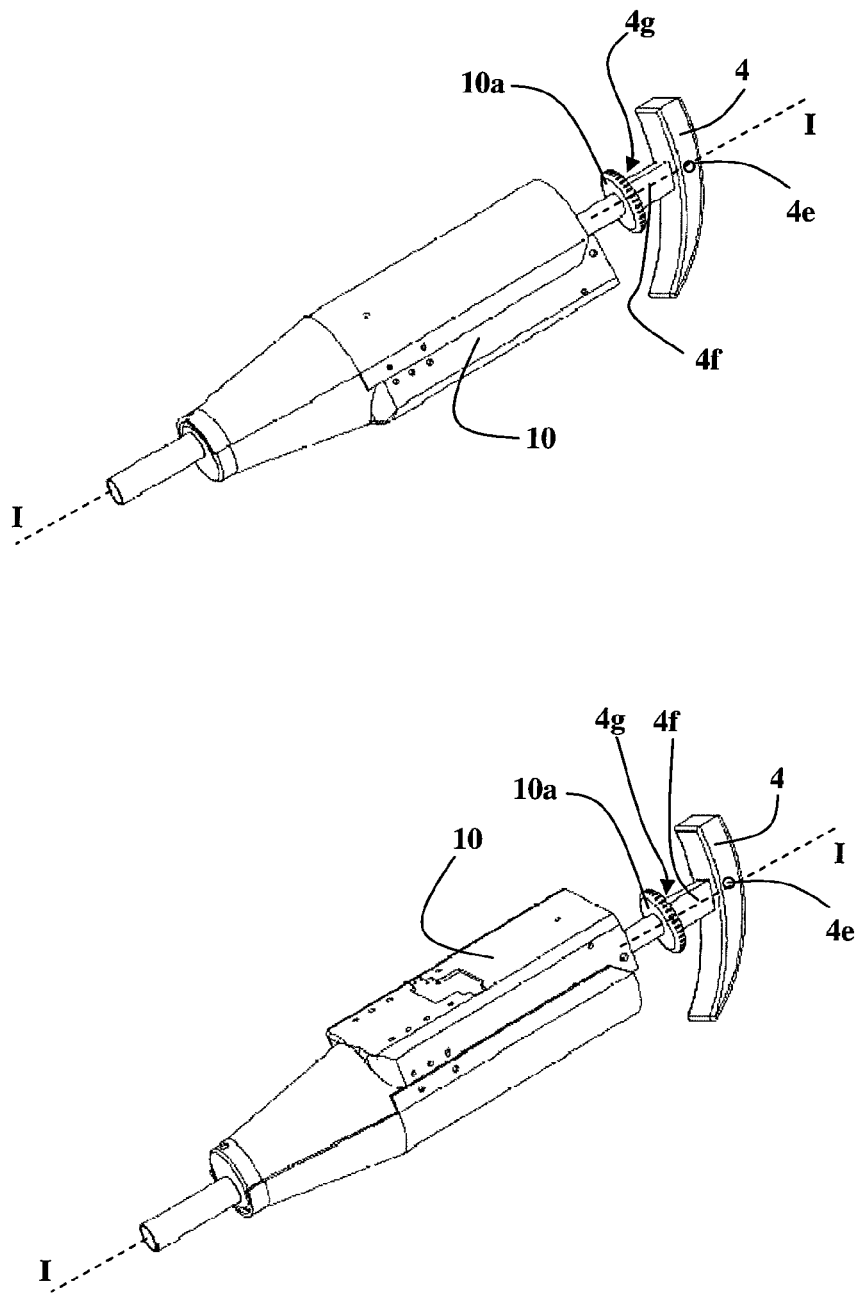
FIG. 22 illustrates two angular positions of the manipulator relative to the handle in a particular embodiment with manual means for orienting the direction of inclination.
Figure 23:
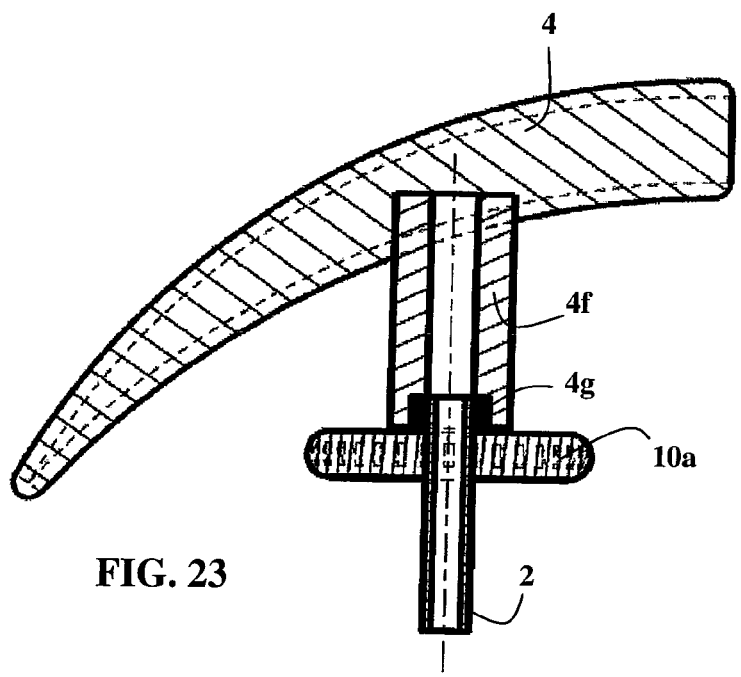
FIG. 23 is a partial side sectional view of the manual orientation means of FIG. 22.
Figure 24:
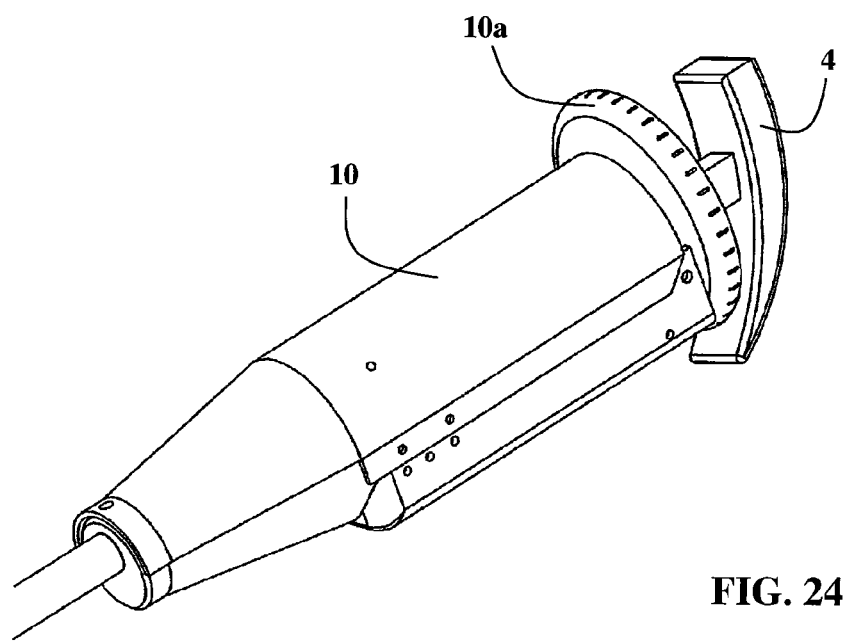
FIG. 24 is a perspective view of the manual orientation means according to a variant of the invention.

As a variant to this first case, the rotation of the connecting arm 2 may be obtained, as illustrated in FIGS. 22 to 24, by providing a joint for axial rotation relative to the handle 4 on the remainder of the manipulator, with means for indexing the position relative to the handle 4. In practice, it is possible to provide that the handle 4 is mounted on a handle support 4f which is itself articulated in axial rotation relative to the control body 10. Preferably, the control body comprises a gripping part 10a which the operator is able to activate to produce the relative rotation of the handle 4 and the control body 10.

Figure 11:
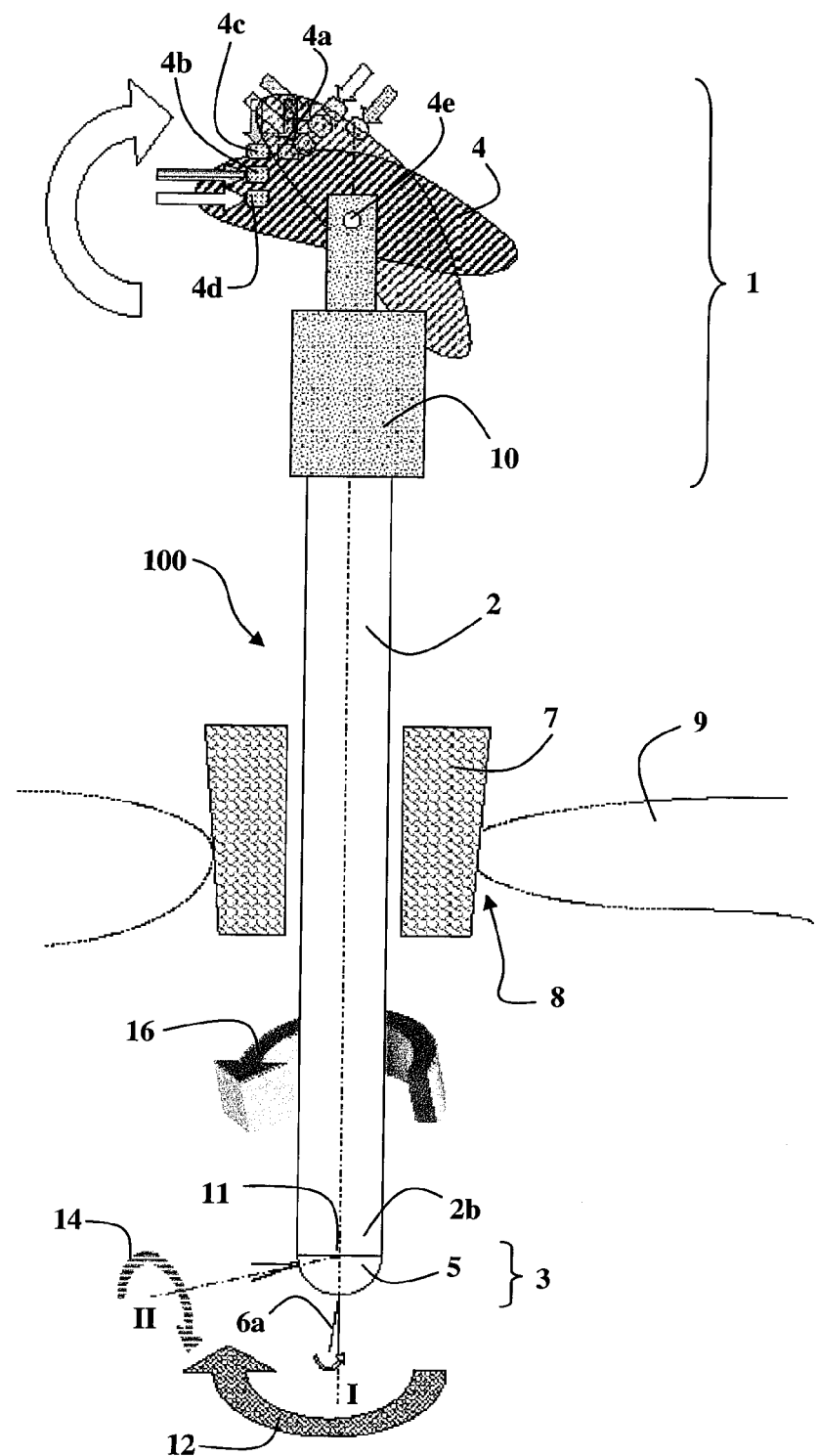
FIG. 11 illustrates an advantageous embodiment for obtaining the movements of the tool.

In the second case, to permit easy axial rotation of the entire manipulator 100 by manipulation of the single handle 4, the handle 4 is itself articulated about an axis of articulation of the handle 4e as illustrated in FIG. 11.

Thus, in FIG. 7, a first embodiment of the manipulator 100 has been illustrated, according to which the handle 4 comprises a first control member 4a of which the actuation causes the motorized inclined movement 12 of the tool support 5, a second control member 4b of which the actuation causes the specific rotational movement 14 of the tool support 5 about its direction of inclination II and a third control member 4c to produce the specific rotational movement 16 of the connecting arm 2 about its longitudinal axis I-I. In this manner, it is possible to orientate the tool 6 in all directions of a cone covering the distal end 2b of the connecting arm 2.

Furthermore, in the embodiment of FIG. 7, as the tool 6 is forceps, the handle 4 comprises a forceps control member 4d, providing the control of the forceps clamping movement illustrated by the arrow 60. In practice, the clamping 60 of the forceps may be implemented by the actuation of the forceps control member 4d which controls the rotation of a forceps actuator 40d housed in the control unit 10 (FIG. 17).

According to the variant illustrated in FIG. 11, the connecting arm 2 is fixed to the control body 10 whilst the handle 4 is articulated about an axis of articulation 4e. In this case, the specific rotational movement 16 is obtained by rotation R (FIG. 20) of the entire control unit 1—connecting arm 2, the rotation R being produced by the hand of the operator who holds the handle 4. Such a rotation R is illustrated by the series of views of FIG. 20. The joint of the handle 4 allows the hand to maintain a correct grip of the handle 4 without exaggerated movement of the joint of the handle, during a sufficient rotation of the manipulator about the longitudinal axis I-I. The other movements of the tool support 5 are obtained in a motorized manner, as in the embodiment of FIG. 7.

Figure 8:
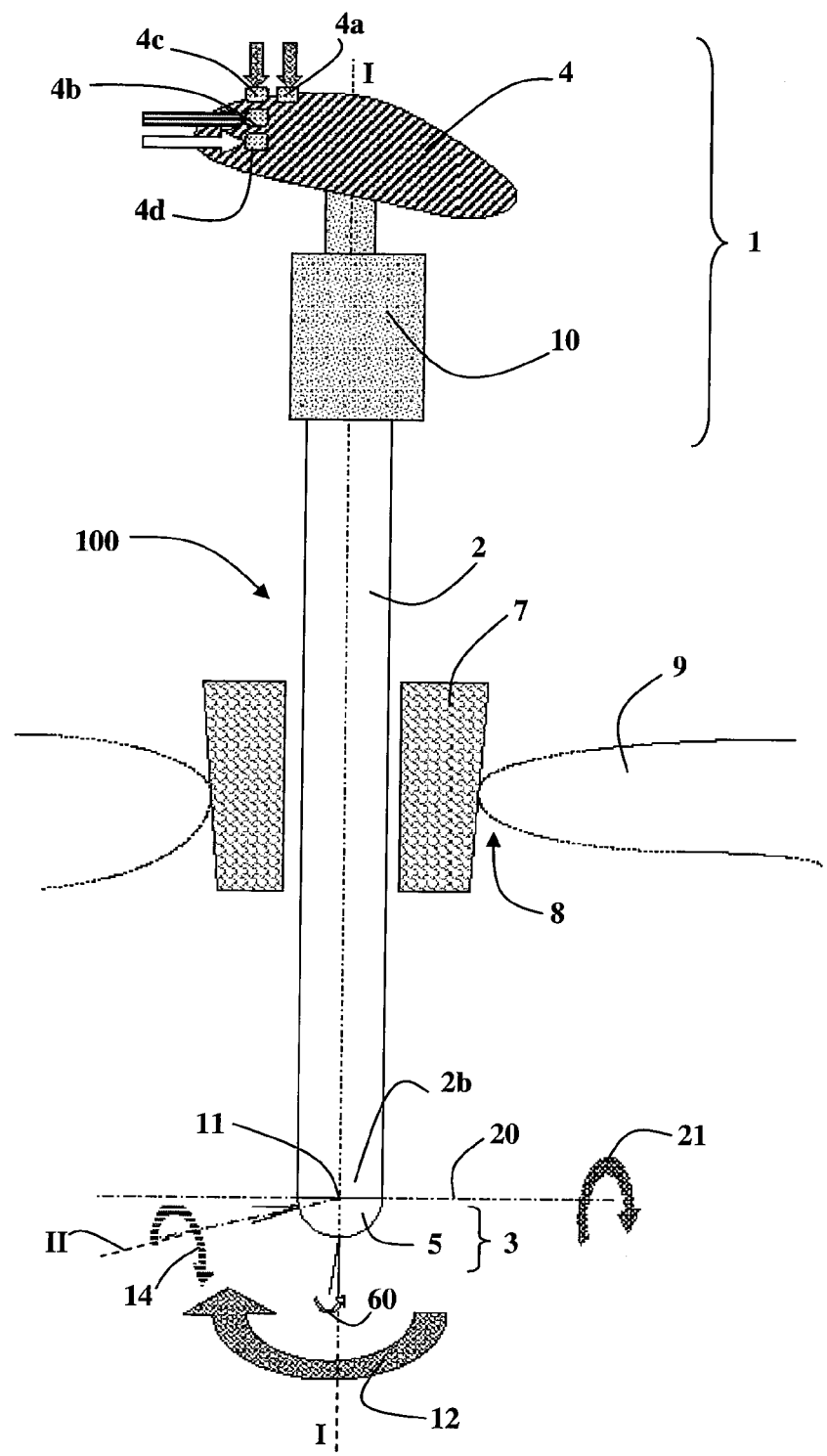
FIG. 8 illustrates a further embodiment for obtaining the movements of the tool.

In the embodiment of FIG. 8, the orientation movement of the direction of inclination II about the longitudinal axis I-I of the connecting arm 2 is obtained by activation of the third control member 4c of the handle 4, which controls a second inclination actuator located in the control body 10, which actuator drives the tool support 5 in rotation along an intersecting transverse axis which is perpendicular to the transverse axis of inclination 11 and the longitudinal axis I-I. Said second transverse axis of articulation is denoted by the reference numeral 20 in FIG. 8 and the rotation is illustrated by the arrow 21.

Thus, by combining the two inclined rotations about the axes 11 and 20, it is possible to orientate the tool 6 in all orientations within a cone covering the distal end 2b of the connecting arm 2.

The other movements of the tool support 5 are identical to those of FIGS. 7 and 11 and are motorized in the same manner.

Figure 9:
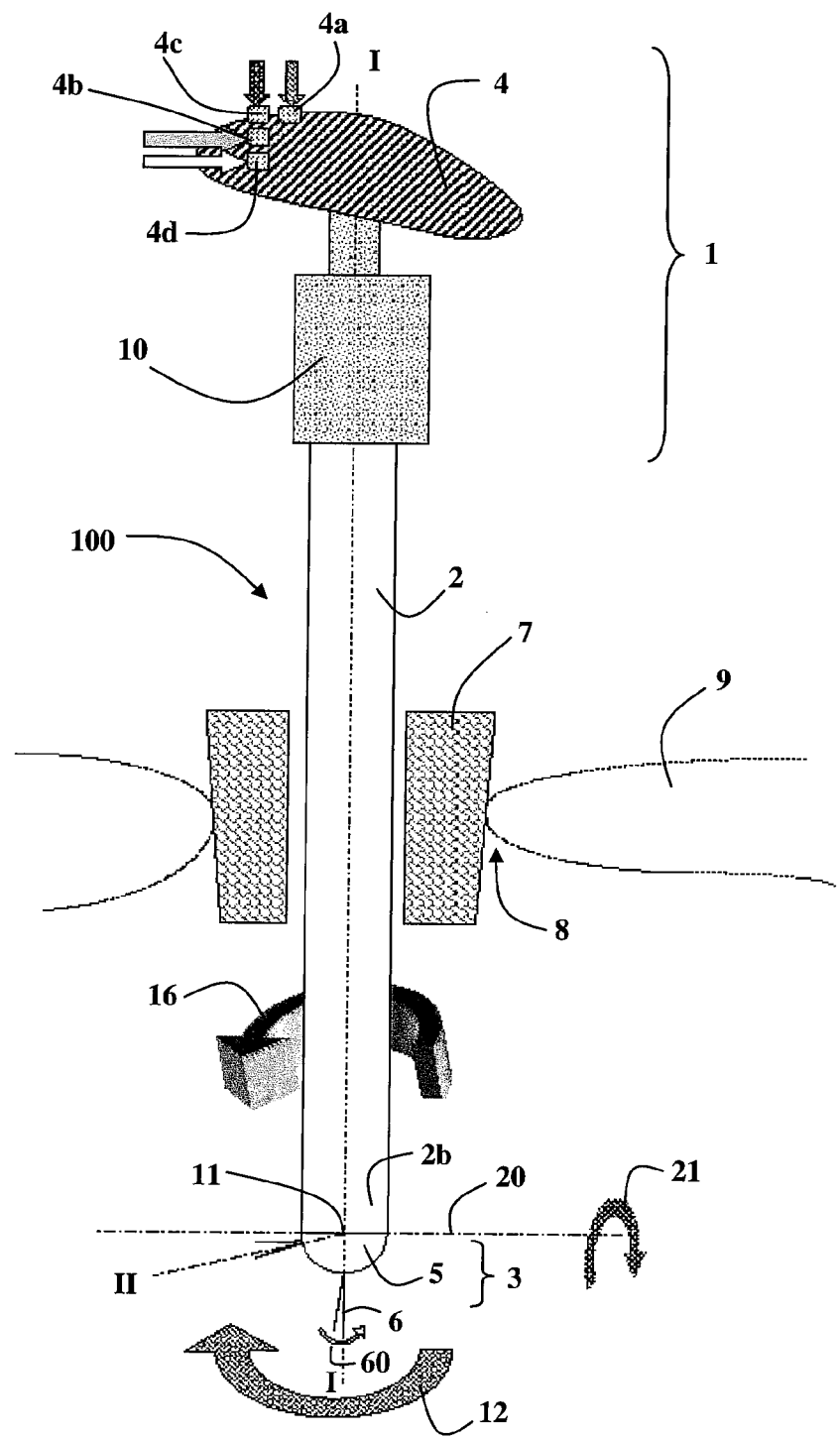
FIG. 9 illustrates a further embodiment for obtaining the movements of the tool.

The first inclined movement 12 about the transverse inclination axis 11, the forceps clamping movement 60 for the tool 6, the second movement of inclination by rotation 21 about a second intersecting transverse axis 20 and the specific rotational movement 16 of the connecting arm 2 about its longitudinal axis I-I are in the embodiment illustrated in FIG. 9. In this case, it is not essential to provide further means to ensure the specific rotation of the tool 6 about its direction of inclination II as this movement may be carried out by the synchronous combination of rotations about the axes 11, 20 and I-I.

Figure 10:
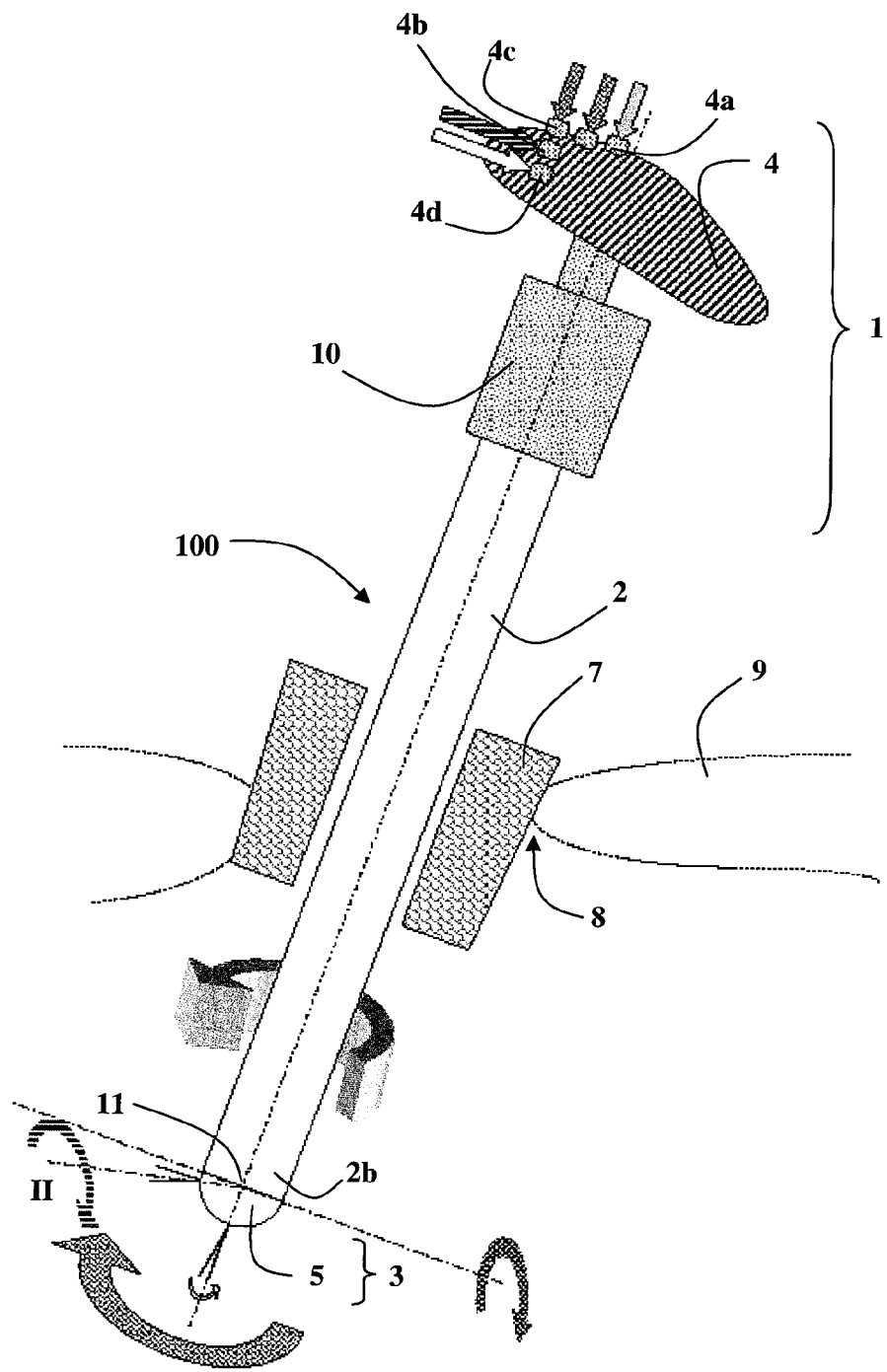
FIG. 10 illustrates a further embodiment for obtaining the movements of the tool.

However, a specific rotational movement of the tool 6 about its inclination axis II may advantageously be added, as illustrated in FIG. 10.

Figure 12:
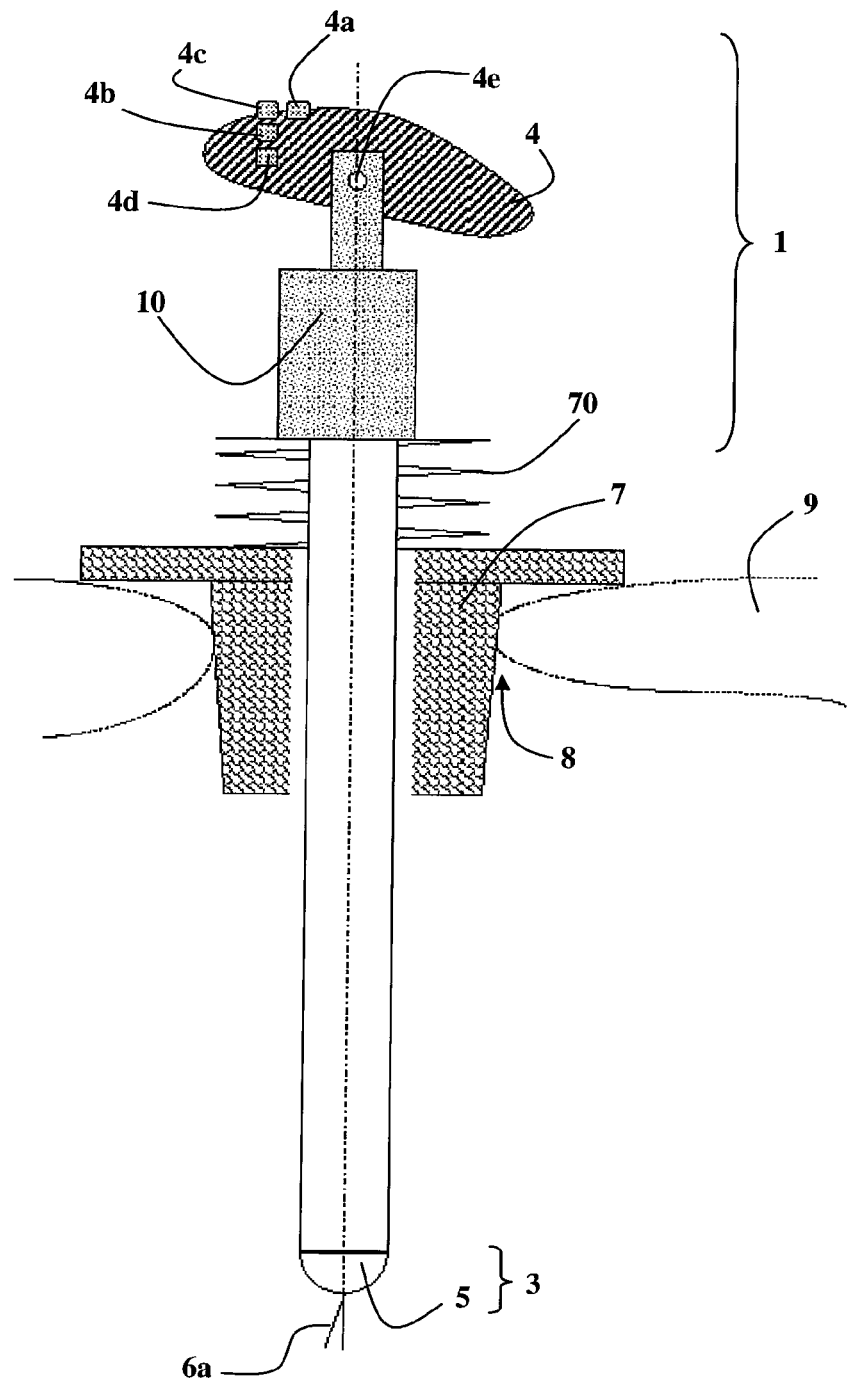
FIG. 12 illustrates a further embodiment of the manipulator with a resilient axial return means between the trocar and the manipulator body.

FIG. 12 illustrates a variant in which a resilient compression system 70 is interposed between the trocar 7 and the control body 10, to relieve the operator of part of the weight of the manipulator.

In all the embodiments disclosed above, the control members 4a-4d may be of the push-button, or touch button, type or any other type of device which is able to be actuated by a finger along a short path and using a small actuating force. In this manner, the risk of interference is further reduced between the actuation of the control members and the holding in position of the entire manipulator by the hand which carries the handle 4.

According to an advantageous embodiment, illustrated by FIG. 27, the second control member 4b comprises a first input member H, of which the actuation causes the specific rotation of the tool support 5 in a first clockwise rotation and a second input member AH, of which the actuation causes the specific rotation of the tool support 5 in a second counter-clockwise direction of rotation. For example, the input members H and AH may be two push-buttons.

Said push-buttons H and AH may each control the rotation of the tool support 5 according to a speed of rotation which is substantially constant.

Alternatively, the push-buttons may be of the progressive type, each controlling the rotation of the tool support 5 according to a variable rotational speed between a rapid speed and a slow speed.

According to a further possibility which is more advantageous, permitting in particular the preparatory stages of adapting the manipulator before an operating movement to be shortened, the buttons may be push-buttons of the "all or nothing" type in stepped mode, changing to continuous mode at higher speeds when maintaining the actuation.

As regards the first control member 4a, it may be advantageously produced in the form of a third input member D, of which the activation causes a positive increase in the angle of inclination, and a fourth input member G, of which the activation causes a negative increase in the angle of inclination. For example, there may be two push-buttons G and D which each control a motor in one respective rotational direction, and the motor stops when the buttons G and D are released.

Advantageously, it is also possible to provide the possibility of activation for rapid resetting, which returns the tool support 5 into the axis of the connecting arm 2, for example if the two push-buttons G and D are pressed simultaneously.

As regards the forceps control member 4d, it is possible to produce it, for example, in the form of a ratchet-type push-button, which controls the clamping of the forceps following a first activation by pressing, and which controls the opening of the forceps following a second activation by pressing, controlling the forceps actuator 40d in both rotational directions.

Advantageously, it is possible to control the forceps actuator with a forceps control member 4d having a first open forceps position, a second forceps position closed by light clamping and a third forceps position closed by strong clamping. This permits the operator, for example, to place a needle in the forceps, to control the light clamping to perfect the positioning of the needle by sliding into the forceps, and then to lock the needle in position by controlling the strong clamping.

Figure 13:
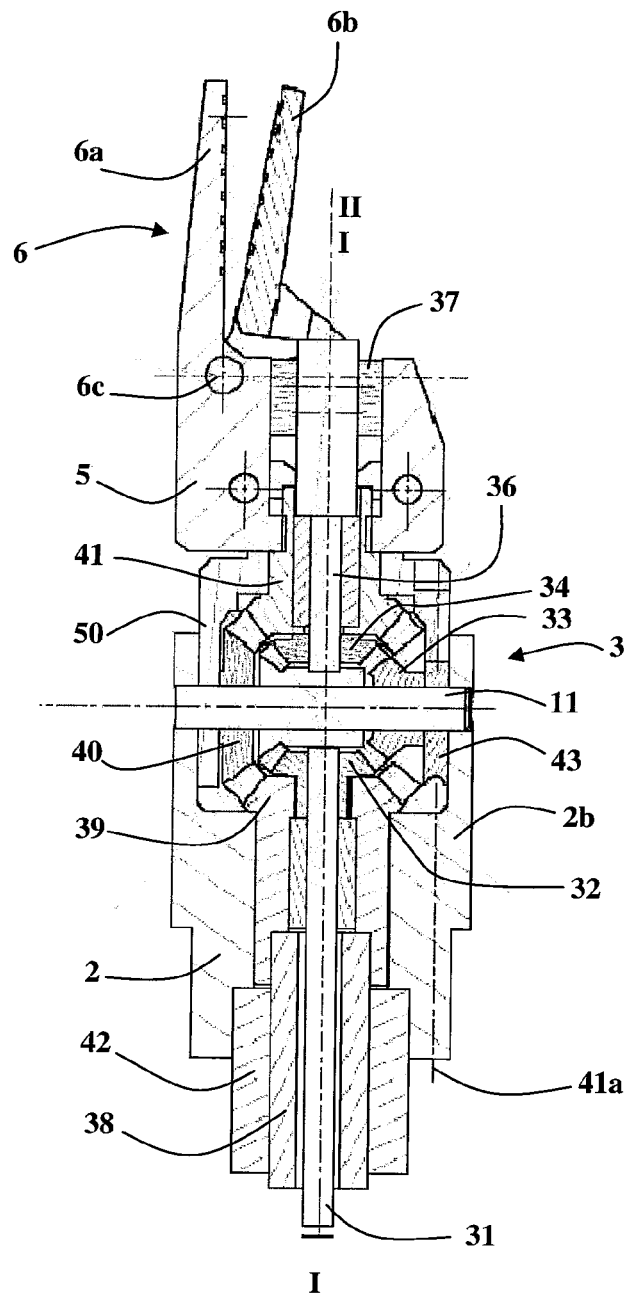
FIG. 13 is a side sectional view illustrating a working unit according to an embodiment of the present invention.
Figure 14:
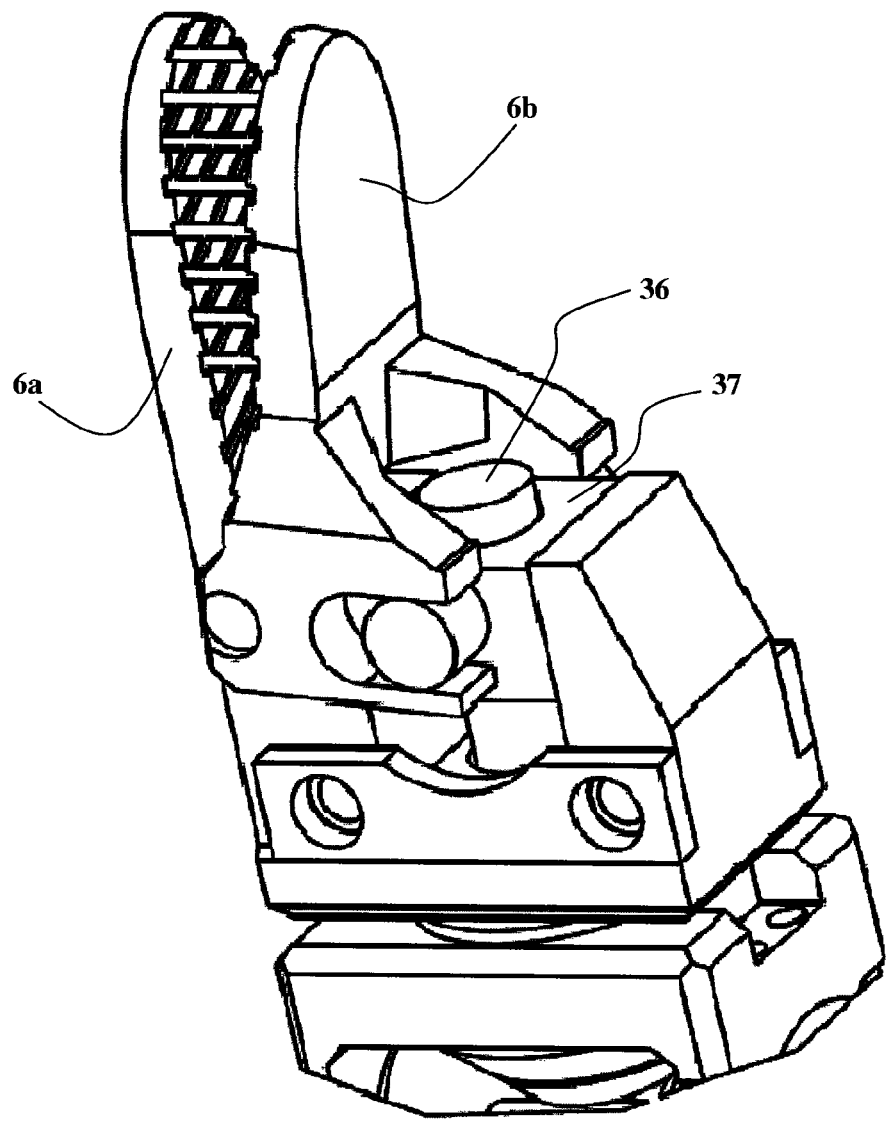
FIG. 14 is a perspective view partially illustrating the working unit according to FIG. 13.
Figure 15:
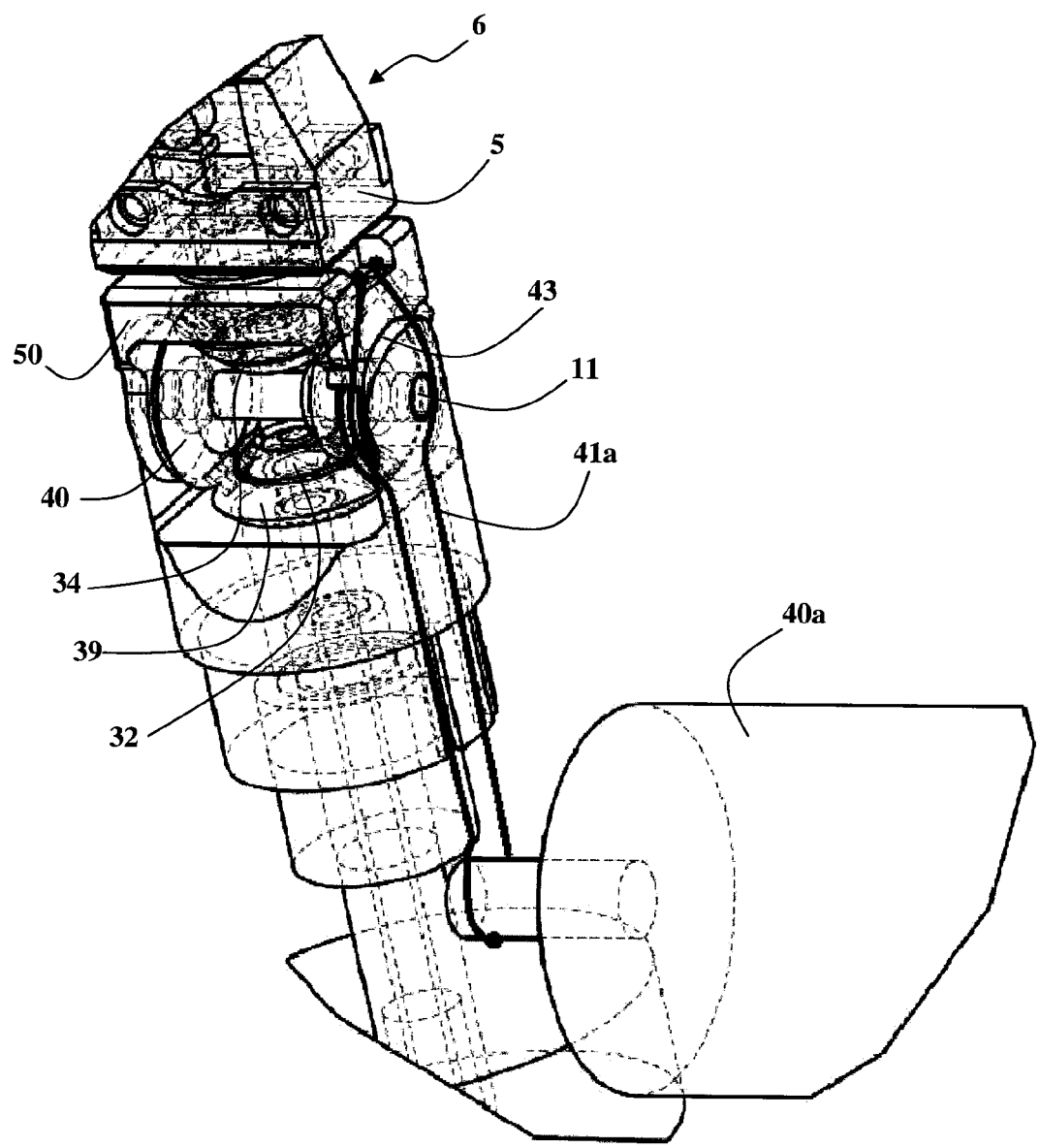
FIG. 15 illustrates an embodiment of the means for driving the tool support in an inclined manner.
Figure 16:
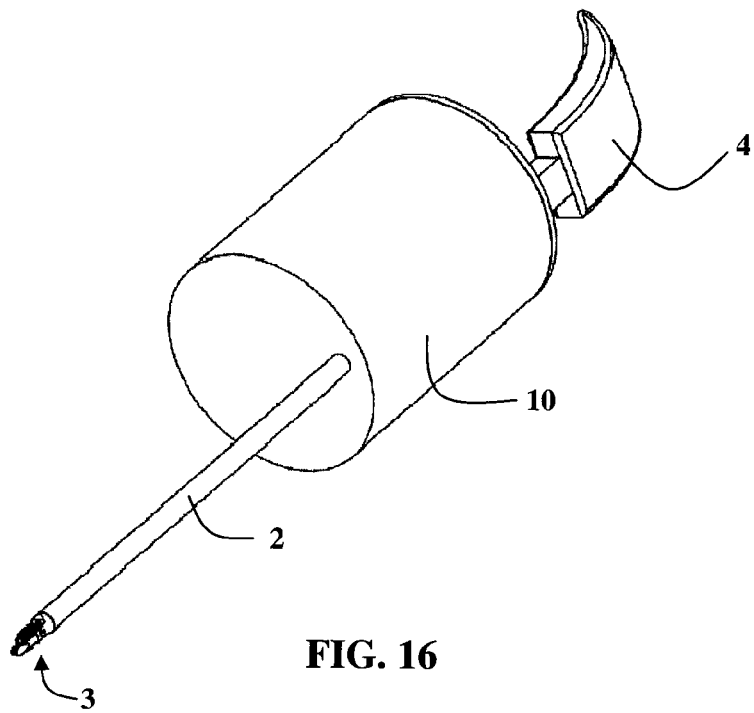
FIG. 16 is an overall perspective view of a manipulator according to an embodiment of the invention.

Now FIGS. 13 and 15 will be considered which illustrate an embodiment of the working unit 3, in the case of a forceps-type tool 6 having a fixed jaw 6a and a mobile jaw 6b about a transverse axis of rotation 6c.

An axial input shaft 31 is provided for the clamping or unclamping movement of the forceps 6, said axial input shaft being coupled to the forceps actuator, being oriented along the longitudinal axis I-I of the connecting arm 2, carrying a conical end pinion 32 which drives a lateral conical pinion 33 rotating about a transverse axis 11 and driving the conical pinion 34 which is itself mounted at the end of a threaded and axially wedged output shaft 36. A nut 37 is mounted on the threaded part of the output shaft 36 and is axially displaced during the rotation of the output shaft 36 to drive the mobile jaw 6b of the tool 6 pivotably about the transverse rotational axis 6c.

The specific rotation of the tool 6 about the axis of inclination II is provided by an input tube 38 oriented along the longitudinal axis I-I, driven in turn in rotation by the specific rotation actuator, and fixed to a conical end pinion 39 which itself drives in rotation a lateral conical pinion 40 rotating about a transverse axis 11 and which drives an axial tubular conical pinion 41 fixed to the tool support 5 (fixed to the fixed jaw 6a in the present case). In other words, the tool 6 is mounted with its fixed jaw 6a in the fixed position on the pinion 41, which itself is mounted axially rotatably in the arched portion 50. A bushing 42 guides the input tube 38 in its rotation about the axis I-I in the connecting arm 2.

The arched portion 50 is pivotably mounted about the transverse axis 11 on the distal end 2b of the connecting arm 2. In its rotation, the arched portion 50 is fixed to a pulley 43 urged in rotation by a cable 41a, more clearly visible in FIG. 15.

As may be seen in FIGS. 15 and 17, the inclination actuator 40a, of the motorized type, causes by its rotation the driving of the cable 41a and the pulley 43 for the inclination of the arched portion 50 and the tool support 5 about the transverse axis 11 as far as a direction of inclination II.

The specific rotation actuator 40b ensures the specific rotation of the tool support 5 about the direction of inclination II, by driving the input tube 38. The forceps actuator 40d ensures the clamping of the forceps 6 by rotation of the input shaft 31.

In FIG. 17 an actuator is also shown for rotating the arm 40c which is capable of causing the rotation of the entire manipulator about the handle 4.

Figure 18:
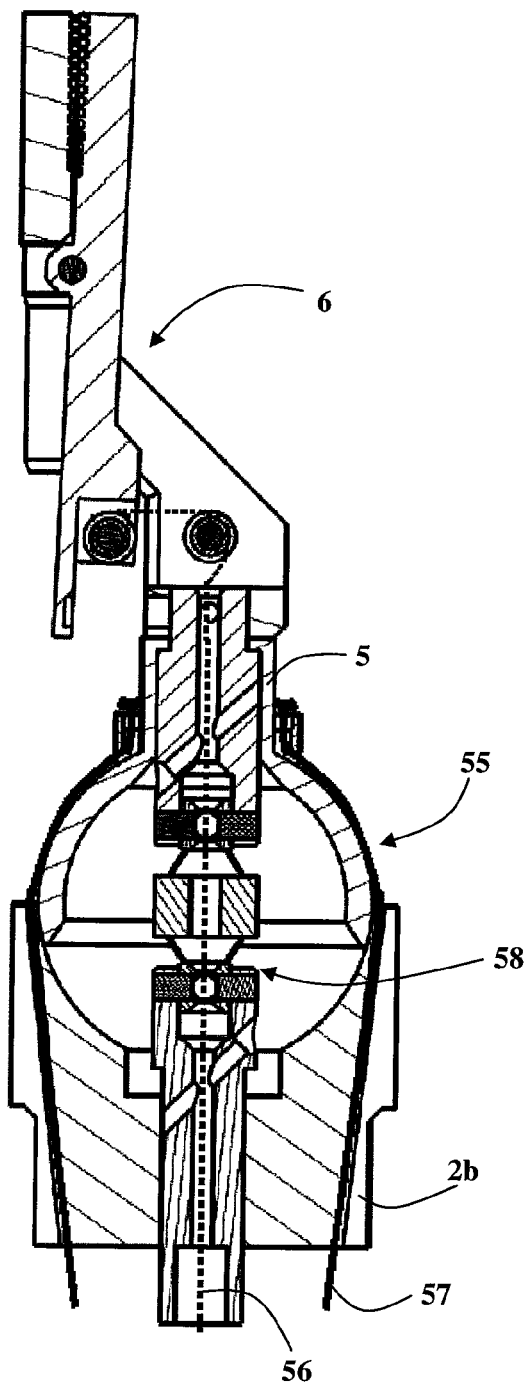
FIG. 18 illustrates, in a sectional side view, the means for transmitting movements in a further embodiment of a working unit of the invention.

In the embodiment illustrated in FIG. 18, the tool support 5 is rotatably mounted according to a spherical joint 55 on the distal end 2b of the connecting arm 2. The oriented driving of the tool support 5 is provided by peripheral cables 57 for pivoting in all possible orientations of the sphere.

The transmission of the clamping movement of the forceps 6 takes place by a central cable 56 whilst the specific rotational movement is carried out by transmission by a universal joint 58. It is possible to consider the description of the French pending patent application No. 2 927 011 which is incorporated here by way of reference.

Figure 19:
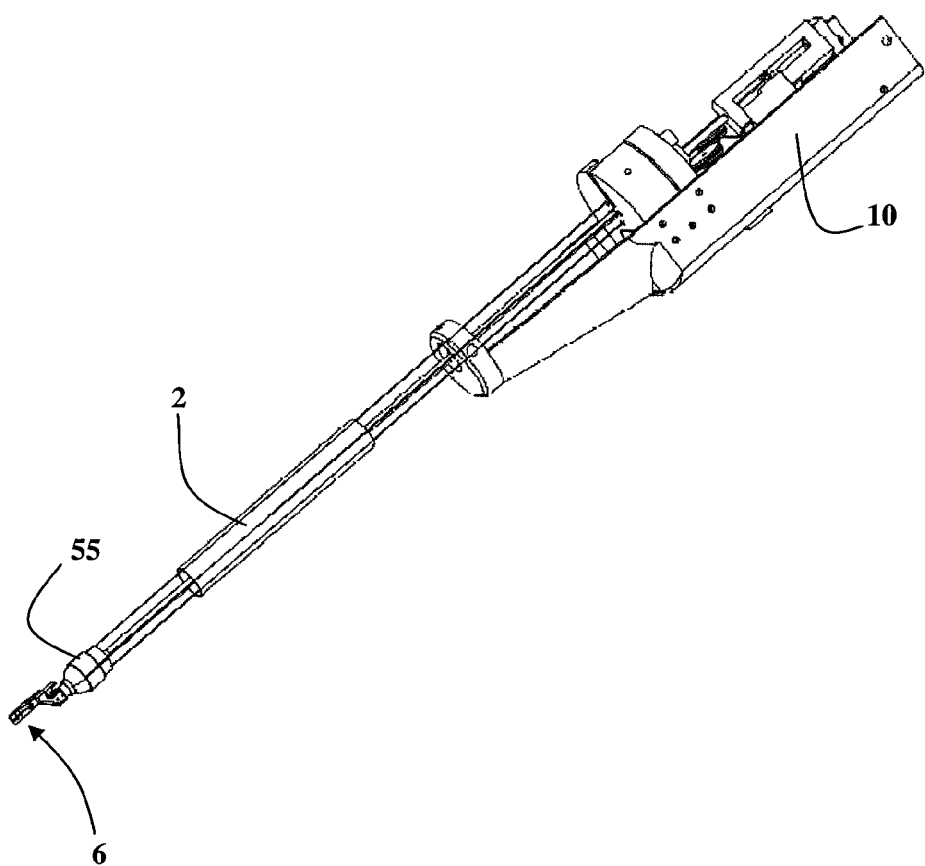
FIG. 19 is an overall perspective, schematic view of a manipulator according to the embodiment of the invention.

In FIG. 19 may be seen the entire manipulator according to this embodiment, with cables for the transmission of the movements.

Figure 20:
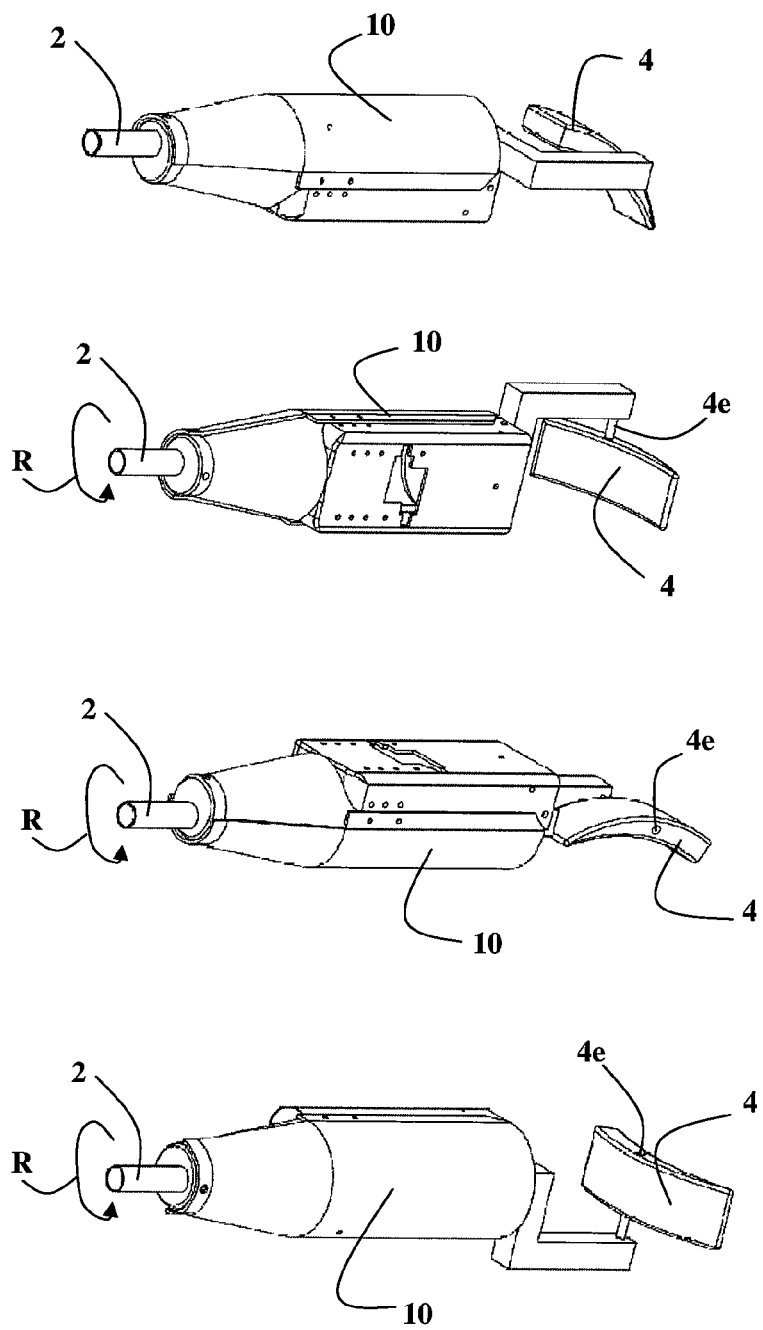
FIG. 20 illustrates the stages of a manual rotational movement of the body of the manipulator using an articulated handle.

FIG. 20 illustrates the specific rotational movement of the manipulator itself, in the case of an embodiment where the specific rotation of the connecting arm 2 is not motorized. Due to the articulation of the handle 4, the hand is able to follow the movements without the fingers being released from the handle 4, ensuring sufficient rotation of the manipulator about its longitudinal axis.

Figure 21:
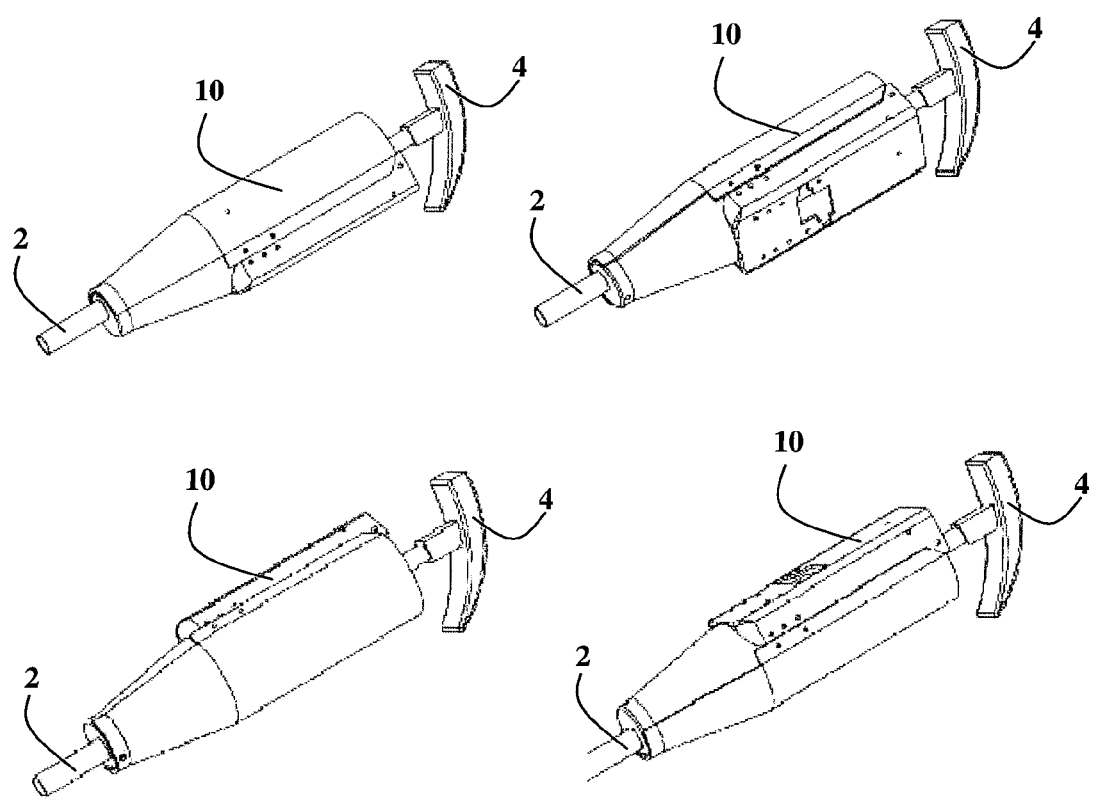
FIG. 21 illustrates in perspective the different stages of a specific motorized axial rotational movement of a manipulator body relative to the handle.

In FIGS. 21 and 17 the embodiment has been illustrated where the control body 10 and the connecting arm 2, which are fixed together, are motorized in rotation relative to the handle 4.

In FIG. 22, the handle 4 is driven manually in axial rotation about the axis I-I due to an axial joint and a gripping part 10a on the control body 10. In practice, the handle 4 is articulated according to the transverse joint 4e on a handle support 4f, itself mounted in free axial rotation by an axial joint 4g on the control body 10.

The axial joint 4g and the gripping part 10a form a member for manually driving in rotation the handle 4 relative to the remainder of the manipulator about the longitudinal axis I-I of the connecting arm 2. The activation of the gripping part 10a by a finger of the hand holding the handle 4, or by a different hand, is useful for carrying out rotations of large amplitude for the orientation of the direction of inclination II about the axis I-I. Rotations of small amplitude, during the operating movement, are carried out ergonomically by manual activation of the handle 4 in rotation.

In the variant illustrated in FIG. 23, the handle 4 is attached and fixed to the handle support 4f. The joint 4g is a bearing of which the external race is fixed to the handle support 4 and of which the internal race is fixed to the connecting arm 2 and the gripping part 10a in the form of a thumbwheel attached to the connecting arm 2.

Alternatively, in the variant illustrated in FIG. 24, the gripping part 10a is directly fixed to the control body 10.

In FIGS. 25 and 26, the handle 4 is connected to the control body 10 by a positioning arm 30 which may be used independently of the other features described here. By means of this positioning arm 30, the handle 4 may be oriented differently or even offset at a distance from the longitudinal axis I-I of the manipulator, for more ergonomic gripping in certain operating conditions.

In FIG. 25, the positioning arm 30 is a semi-rigid rod 5 to 30 cm long, deformable by flexion under flexional or torsional forces greater than the forces produced alone by the weight of the manipulator and the resistance of the tissue treated by the manipulator. The handle 4 may be fixed to the end of the semi-rigid rod 30. Alternatively, it may be articulated according to a transverse axis of articulation 4e.

In FIG. 26, the positioning arm 30 is a rigid rod, carrying at its proximal end the handle 4 with a possible transverse joint 4e, and articulated at its distal end to the control body 10 by a joint 35 which may be locked in position.

As disclosed in some of the preceding embodiments, the handle 4 may advantageously be mounted freely in rotation about an axis of articulation 4e.

For example, the axis of articulation 4e may be a transverse axis relative to the longitudinal axis I-I of the connecting arm 2.

However, it is possible to provide further orientations of the axis of articulation 4e, for example a longitudinal orientation or an oblique orientation, each possibility having respective advantages.

In all embodiments, each of the actuators may be, for example, of the electric motor, hydraulic actuator or pneumatic actuator type. Actuators of the electric motor type are preferable, in particular for the ease of power supply and flexibility of control.

The present invention is not limited to the embodiments which have been specifically described but it incorporates different variants and generalizations contained within the scope of the following claims.

The invention claimed is:

1. A manipulator comprising:
    a control unit (1), having a handle (4) capable of being held by one hand,
    control members (4a-4d) mounted on the handle (4) and capable of being actuated by at least one finger of the hand holding the handle (4),
    a connecting arm (2) extending along a longitudinal axis (I-I), having a proximal end (2a) in which the control unit (1) is mounted, and having a distal end (2b),
    a working unit (3) mounted on the distal end (2b) of the connecting arm (2) and comprising a tool support (5) capable of supporting a tool (6),
    the tool support (5) being mounted in a manner in which it can be inclined in the working unit (3) relative to the connecting arm (2) by rotation about a transverse inclination axis (11),
    the control members (4a-4d) make it possible to control the transverse inclination (12) of the tool support (5) in a direction of inclination (II) by rotation about the transverse inclination axis (11),
    the control members (4a-4d) make it possible to control a specific rotation (14) of the tool support (5) about the direction of inclination (II), and in which:
in a transverse inclined rotation (12), the tool support (5) is driven by at least one first inclination actuator (40a) controlled by a first (4a) of the control members of the handle (4),
in the specific rotational movement (14) of the tool support (5) about the direction of inclination (II), the manipulator is controlled by a second (4b) of the control members of the handle (4) which controls one or more actuators (40b),
wherein the specific rotational movements (14) and possible opening-closing (60) movements of the tool (6) are transmitted to the tool support (5) only by gears (39, 40, 41; 32, 33, 34) and tubes (38, 41) or shafts (31, 36) housed in the working unit (3), whilst the inclination movements about the transverse inclination axis (11) are transmitted by cables (41a).

2. The manipulator as claimed in claim 1, wherein the specific rotational movement (14) of the tool support (5) is provided by an input tube (38) oriented along the longitudinal axis (I-I), in turn driven in rotation by a specific rotation actuator (40b) and carrying a conical end pinion (39) which itself drives in rotation a lateral conical pinion (40) rotating about a transverse axis (11) and which drives an axial conical pinion (41) fixed to the tool support (5).

3. The manipulator as claimed in claim 1, in which the tool (6) is forceps, wherein:
a forceps actuator is coupled to an axial input shaft (31) oriented along the longitudinal axis (I-I) of the connecting arm (2),
the axial input shaft (31) carries a conical end pinion (32) which drives a lateral conical pinion (33) rotating about a transverse axis (11) and driving a conical pinion (34) mounted at the end of an axially threaded and wedged output shaft (36) on which is mounted a nut (37) fixed to a mobile jaw (6b) of the forceps (6).

4. The manipulator as claimed in claim 3, wherein the forceps comprise a fixed jaw (6a) and a mobile jaw (6b).

5. The manipulator as claimed in claim 1, wherein the tool support (5) comprises an arched portion (50) pivotably mounted about a transverse axis (11) on the distal end (2b) of the connecting arm (2) and fixed to a pulley (43) urged in rotation by a cable (41a) which is itself activated by the first inclination actuator (40a).

6. The manipulator as claimed in claim 1, wherein the second (4b) of the control members comprises a first input member (H), of which the actuation causes the specific rotation of the tool support (5) in a first rotational direction and a second input member (AH), of which the actuation causes the specific rotation of the tool support (5) in the second rotational direction.

7. The manipulator as claimed in claim 1, wherein the first (4a) of the control members comprises a third input member (D), of which the activation causes an increase in the inclination angle, and a fourth input member (G), of which the activation causes a decrease in the inclination angle.

8. The manipulator as claimed in claim 6, wherein the input members comprise discrete on or off members and each control the movement of the tool support (5) in one respective direction according to a substantially constant rotational speed.

9. The manipulator as claimed in claim 6, wherein the input members are continuously adjustable, each controlling the movement of the tool support (5) according to a rotational speed which is variable between a rapid speed and a slow speed.

10. The manipulator as claimed in claim 6, wherein the input members comprise discrete on or off members in stepped mode, changing to continuous mode at higher speeds by maintaining the activation.

11. The manipulator as claimed in claim 7, wherein the first (4a) of the control members can activate resetting, which returns the transverse inclination (12) of the tool support (5) into alignment with the longitudinal axis (I-I).

12. The manipulator as claimed in claim 1, wherein in the case of a forceps-type tool (6), the manipulator also comprises on the handle (4) a forceps control member (4d), of which the actuation controls at least one forceps actuator (40d).

13. The manipulator as claimed in claim 12, wherein the forceps control member (4d) comprises a first open forceps position, at least one second forceps position closed by light clamping and at least one third forceps position closed by strong clamping.

14. The manipulator as claimed in claim 1, comprising an actuator for rotating the arm (40c), carrying out the specific rotation of the connecting arm (2) about its longitudinal axis (I-I) relative to the handle (4), said actuator for rotating the arm being controlled by the third control member (4c) of the handle (4).

15. The manipulator as claimed in claim 1, wherein the drive member of the handle (4) relative to the remainder of the manipulator comprises an axial joint (4g) between the connecting arm (2) and the handle (4) and comprises a thumbwheel defining a gripping part (10a) attached to the connecting arm (2) or to the control body (10).

16. The manipulator as claimed in claim 1, comprising, between the handle (4) and the connecting arm (2), a positioning arm (30) by which the operator is able to modify and fix the angular and/or spatial position relative to the handle (4) with regard to the connecting arm (2).

* * * * *